(12) United States Patent
Habeck et al.

(10) Patent No.: US 6,545,174 B2
(45) Date of Patent: Apr. 8, 2003

(54) COSMETIC AND PHARMACEUTICAL PREPARATIONS CONTAINING PHOTOSTABLE UV FILTERS

(75) Inventors: Thorsten Habeck, Meckenheim (DE); Sylke Haremza, Neckargemünd (DE); Volker Schehlmann, Römerberg (DE); Horst Westenfelder, Neustadt (DE); Thomas Wünsch, Speyer (DE); Michael Drögemüller, Mannheim (DE); Volker Bomm, Neunkirchen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/765,624

(22) Filed: Jan. 22, 2001

(65) Prior Publication Data

US 2002/0016310 A1 Feb. 7, 2002

Related U.S. Application Data

(62) Division of application No. 09/133,173, filed on Aug. 13, 1998, now Pat. No. 6,238,649.

(30) Foreign Application Priority Data

Aug. 13, 1997 (DE) .......................... 197 35 093
Oct. 22, 1997 (DE) .......................... 197 46 654
Dec. 15, 1997 (DE) .......................... 197 55 649

(51) Int. Cl.[7] ...................... C07C 69/76; C07C 233/00
(52) U.S. Cl. .......................... 560/76; 564/152
(58) Field of Search ............... 562/468, 480; 560/57; 424/59

(56) References Cited

U.S. PATENT DOCUMENTS 6,191,301 B1 * 2/2001 Habeck et al.

OTHER PUBLICATIONS

Martelli et al, Reactions Avec le Diazomethane d'Esters Cinnamylidene Maloniques ou Cyanacetiques et Des Malononitriles Correspondants: Themolyse Des Pyrazolines Obtenus, 1977, Bulletin de la Societe Chimique de France, (11–12, Pt. 2), pp. 1182–1186.*

Kato et al, Studies on ketene and Its Derivatives. XCII. Reaction of Diketene with Benzaldehyde, Cinnamaldehyde and beta–Phenylcinnamaldehyde, 1978, Chemical and Pharmaceutical Bulletin, 26(12), pp. 3877–3879.*

Kato et al, Reaction of Diazomethane with 2–Acetyl–5, 5–diphenyl–2,4–entadienoic Acid and Related Compounds, 1976, Chemical and Pharmaceutical Bulletin, 24(12), pp. 3034–3038.*

English Translation of Martelli et al, 1977, Bulletin de la Societe Chimique de France, (11–12, Pt. 2), pp. 1182–1186.*

* cited by examiner

Primary Examiner—Johann Richter
Assistant Examiner—Paul A. Zucker
(74) Attorney, Agent, or Firm—Keil & Weinkauf

(57) ABSTRACT 4,4-Diarylbutadienes of the formula I,

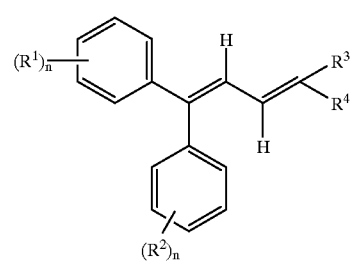

where the diene system has the Z,Z; Z,E; E,Z or E,E configuration or a mixture thereof, and where the variables independently of one another have the following meanings: $R^1$ and $R^2$ are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted, substituents which confer solubility in water and are selected from the group consisting of carboxylate, sulfonate, or ammonium residues; $R^3$ is $COOR^5$, $CONR^5R^6$; $R^4$ is $COOR^6$, $CONR^5R^6$; $R^5$ and $R^6$ are hydrogen, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted; n is 1 to 3; and $R^3$ and $R^4$ are not $COOCH_3$ when $R^1$ and $R^2$ are hydrogen, are used as photostable UV filters in cosmetic and pharmaceutical preparations to protect the human skin or human hair from the sun's rays, alone or together with compounds which absorb in the UV region and are known per se for cosmetic and pharmaceutical preparations.

3 Claims, No Drawings

COSMETIC AND PHARMACEUTICAL PREPARATIONS CONTAINING PHOTOSTABLE UV FILTERS

This application is a divisional application of Ser. No. 09/133,173, filed Aug. 13, 1998 now U.S. Pat. No. 6,238,649.

The invention relates to the use of 4,4-diarylbutadienes as photostable UV filters in cosmetic and pharmaceutical preparations for protecting the human epidermis or human hair from UV radiation, specifically in the range from 320 to 400 nm.

The sunscreens employed in cosmetic and pharmaceutical preparations have the task of preventing, or at least diminishing the consequences of, the harmful effects of sunlight on the human skin. However, these sunscreens also serve to protect other ingredients from decomposition or breakdown by UV radiation. The intention in hair cosmetic formulations is to reduce damage to the keratin fibers by UV rays.

The sunlight reaching the surface of the earth contains UV-B radiation (280 to 320 nm) and UV-A radiation (>320 nm), which are directly adjacent to the visible light region. The effect on the human skin is manifested, particularly with UV-B radiation, by sunburn. Accordingly, the industry supplies a relatively large number of substances which absorb UV-B radiation and thus prevent sunburn.

Dermatological investigations have now shown that UV-A radiation is also perfectly able to cause skin damage and allergies by, for example, damaging the keratin or elastin. This reduces the elasticity and water storage capacity of the skin, ie. the skin becomes less supple and tends to form wrinkles. The noticeably high incidence of skin cancer in regions where the sun's radiation is strong shows that damage to the genetic information in the cells is evidently also caused by sunlight, specifically by UV-A radiation. All these findings therefore make it appear necessary to develop efficient filter substances for the UV-A region.

There is a growing demand for sunscreens for cosmetic and pharmaceutical preparations which can be used in particular as UV-A filters and whose absorption maxima ought therefore to be in the range from about 320 to 380 nm. In order to achieve the required effect by using the minimum amount, sunscreens of this type ought additionally to have a high specific extinction. Sunscreens for cosmetic products must also meet a large number of other requirements, for example good solubility in cosmetic oils, high stability of the emulsions produced with them, toxicological acceptability, and slight intrinsic odor and little intrinsic color.

Another requirement which sunscreens must meet is adequate photostability. However, this is only inadequately ensured, if at all, with UV-A-absorbing sunscreens hitherto available.

French Patent No. 2 440 933 describes 4-(1,1-dimethylethyl)-4'-methoxydibenzoylmethane as UV-A filter. It is proposed to combine this specific UV-A filter, which is sold by GIVAUDAN under the name "PARSOL 1789", with various UV-B filters in order to absorb all UV rays with a wavelength from 280 to 380 nm.

However, this UV-A filter does not have sufficient photochemical stability, when it is used alone or in combination with UV-B filters, to ensure sustained protection of the skin during lengthy sunbathing, which means that repeated applications at regular and short intervals are required if effective protection of the skin from all UV rays is desired.

For this reason, EP-A-0 514 491 discloses the stabilization of insufficiently photostable UV-A filters by adding 2-cyano-3,3-diphenylacrylic esters which themselves act as filters in the UV-B region.

It has furthermore been proposed in EP-A-0 251 398 to combine chromophores absorbing UV-A radiation and UV-B radiation into one molecule by using a linker. This has the disadvantage that a free combination of UV-A and UV-B filters in the cosmetic preparation is no longer possible, and that difficulties in the chemical linkage of the chromophores allow only certain combinations.

U.S. Pat. No. 4,950,467 describes the use of 2,4-pentadienoic acid derivatives as UV absorbers in cosmetic products. The monoaryl-substituted compounds which are mentioned as preferred in this patent likewise have the disadvantage that their photostability is insufficient.

It is an object of the present invention to propose sunscreens for cosmetic and pharmaceutical purposes which absorb in the UV-A region with high extinction, are photostable, have a slight intrinsic color, ie. a sharp band structure, and are soluble in oil or water depending on the substituent.

We have found that this object is achieved by the use of 4,4-diarylbutadienes of the formula I

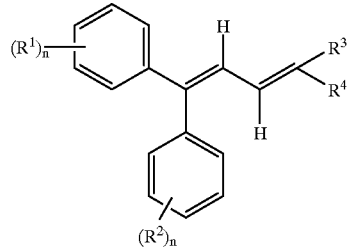

where the diene system has the Z,Z; Z,E; E,Z or E,E configuration or a mixture thereof, and where the variables independently of one another have the following meanings:

$R^1$ and $R^2$ hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted, substituents which confer solubility in water and are selected from the group consisting of carboxylate, sulfonate or ammonium residues;

$R^3$ hydrogen, $COOR^5$, $COR^5$, $CONR^5R^6$, CN, O=S(—$R^5$)=O, O=S(—$OR^5$)=O, $R^7O$—P(—$OR^8$)=O, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted;

$R^4$ $COOR^6$, $COR^6$, $CONR^5R^6$, CN, O=S(—$R^6$)=O, O=S(—$OR^6$)=O, $R^7O$—P(—$OR^8$)=O $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted;

$R^5$ to $R^8$ hydrogen, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted;

n from 1 to 3;

where the variables $R^3$ to $R^8$ may, in each case together with the carbon atoms to which they are bonded, together form a 5- or 6-membered ring which may be further fused, as photostable UV filters in cosmetic and pharmaceutical compositions for protecting the human skin or human hair from the sun's rays, alone or together with compounds which absorb in the UV region and are known per se for cosmetic and pharmaceutical preparations.

Alkyl radicals $R^1$ to $R^8$ which may be mentioned are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals $R^1$ to $R^8$ which may be mentioned are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals which may be mentioned for $R^1$ to $R^8$ are preferably unsubstituted or alkyl-substituted $C_3$–$C_{10}$-cycloalkyl rings such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-2-butylcyclopropyl, 1,2-dimethylcyclopropyl, 1-methyl-2-ethylcyclopropyl, cyclooctyl, cyclononyl or cyclodecyl.

Cycloalkenyl radicals which may be mentioned for $R^1$ to $R^8$ are preferably unsubstituted or alkyl-substituted $C_3$–$C_{10}$-cycloalkenyl rings with one or more double bonds such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkenyl and cycloalkyl radicals may be unsubstituted or substituted by one or more, eg. 1 to 3, radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms such as sulfur, nitrogen, whose free valencies can be saturated by hydrogen or $C_1$–$C_4$-alkyl, or oxygen in the ring.

Bicycloalkyl or bicycloalkenyl radicals which may be mentioned for $R^3$ to $R^8$ are saturated or unsaturated $C_7$–$C_{10}$ bicyclic ring systems, in particular bicyclic terpenes such as pinane, pinene, bornane or camphor derivatives, or adamantane.

Suitable alkoxy radicals for $R^1$ to $R^2$ are those having 1 to 12 carbon atoms, preferably having 1 to 8 carbon atoms.

Examples which may be mentioned are:

| | |
|---|---|
| methoxy- | ethoxy- |
| isopropoxy- | n-propoxy- |
| 1-methylpropoxy- | n-butoxy- |
| n-pentoxy- | 2-methylpropoxy- |
| 3-methylbutoxy- | 1,1-dimethylpropoxy- |
| 2,2-dimethylpropoxy- | hexoxy- |
| 1-methyl-1-ethylpropoxy- | heptoxy- |
| octoxy- | 2-ethylhexoxy- |

Examples of alkoxycarbonyl radicals for $R^1$ and $R^2$ are those containing the abovementioned alkoxy radicals or radicals derived from higher alcohols, eg. having up to 20 carbon atoms, such as iso-$C_{15}$ alcohol.

Suitable mono- or dialkylamino radicals for $R^1$ and $R^2$ are those containing alkyl radicals having 1 to 12 carbon atoms, such as methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl means aromatic rings or ring systems having 6 to 18 carbon atoms in the ring system, for example phenyl or naphthyl, each of which may be unsubstituted or substituted by one or more radicals such as halogen, eg. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Hetaryl radicals are advantageously simple or fused aromatic ring systems having one or more heteroaromatic 3- to 7-membered rings. Heteroatoms which may be present in the ring or ring system are one or more nitrogen, sulfur and/or oxygen atoms.

Hydrophilic radicals, ie. those making it possible for compounds of the formula I to dissolve in water, for $R^1$ and $R^2$ are, for example, carboxyl and sulfo radicals and, in particular, their salts with any physiologically tolerated cations, such as the alkali metal salts or such as the trialkylammonium salts, such as tri(hydroxyalkyl)ammonium salts or the 2-hydroxymethyl-2-propylammonium salts. Also suitable are ammonium radicals, especially alkylammonium radicals, with any physiologically tolerated anions.

Preferred compounds of the formula I are those where $R^1$ and $R^2$ are, independently of one another, hydrogen, $C_1$–$C_{12}$-alkyl, $C_1$–$C_8$-alkoxy, $C_1$–$C_{12}$-alkylamino, $C_1$–$C_{12}$-dialkylamino, substituents which confer solubility in water and are selected from the group consisting of carboxylate, sulfonate or ammonium residues;

$R^3$ is hydrogen, COOR$^5$, COR$^5$, CONR$^5$R$^6$, CN, $C_1$–$C_{12}$-alkyl, $C_3$–$C_6$-cycloalkyl, $C_7$–$C_{10}$-bicycloalkyl, phenyl, naphthyl, thienyl, unsubstituted or substituted;

$R^4$ is COOR$^6$, COR$^6$, CONR$^5$R$^6$, CN, $C_1$–$C_{12}$-alkyl, $C_3$–$C_{10}$-cycloalkyl, $C_7$–$C_{10}$-bicycloalkyl, phenyl, naphthyl, thienyl, unsubstituted or substituted;

$R^5$ and $R^6$ are, independently of one another, hydrogen, $C_1$–$C_{12}$-alkyl, $C_3$–$C_6$-cycloalkyl, $C_7$–$C_{10}$-bicycloalkyl, phenyl, naphthyl, unsubstituted or substituted;

n is from 1 to 3.

$C_1$–$C_{12}$-Alkyl radicals which are particularly preferred for $R^1$ to $R^6$ are methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 2-ethylhexyl.

Cycloalkyl radicals particularly preferred for $R^3$ to $R^6$ are branched or unbranched cyclopentyl and cyclohexyl.

Suitable and particularly preferred alkyl radicals for mono- or dialkylamino for $R^1$ and $R^2$ are methyl, ethyl, n-propyl, n-butyl, 2-methylpropyl, 1,1-dimethylpropyl and 2-ethylhexyl.

Bicycloalkyl radicals particularly preferred for $R^3$ to $R^6$ are camphor derivatives.

The substituents $R^1$ and $R^2$ may each be bonded to the aromatic ring in the ortho, meta and/or para position. In the case of disubstituted aromatic rings (n=2), $R^1$ and $R^2$ can be in the ortho/para or meta/para position. Preferred compounds of the formula I where n=1 are those in which $R^1$ is identical to $R^2$ and both radicals are in the para position.

It is furthermore particularly preferred to use compounds of the formula I where $R^3$ or $R^4$ is not H, CN, $C_1$–$C_{20}$-alkyl, $C_2$–$C_{10}$-alkenyl, aryl, hetaryl, unsubstituted or substituted, when respectively $R^4$ or $R^3$ is $COOR^5$ or $COOR^6$.

Very particularly preferred compounds of the formula I are those where $R^1$ and $R^2$ are independently of one another hydrogen, $C_1$–$C_{12}$-alkyl, $C_1$–$C_8$-alkoxy, substituents which confer solubility in water and are selected from the group consisting of carboxylate, sulfonate or ammonium residues;

$R^3$ is hydrogen, $COOR^5$, $COR^5$, $CONR^5R^6$, CN, $C_3$–$C_6$-cycloalkyl, $C_7$–$C_{10}$-bicycloalkyl;

$R^4$ is $COOR^6$, $COR^6$, $CONR^5R^6$, CN, $C_3$–$C_6$-cycloalkyl, $C_7$–$C_{10}$-bicycloalkyl, where $R^3$ or $R^4$ is not $COOR^5$ or $COOR^6$ when $R^4$ is CN or $R^3$ is hydrogen or CN;

$R^5$ and $R^6$ are independently of one another hydrogen, $C_1$–$C_{12}$-alkyl, $C_3$–$C_6$-cycloalkyl, $C_7$–$C_{10}$-bicycloalkyl, phenyl, naphthyl, unsubstituted or substituted;

n is from 1 to 3.

Furthermore, compounds of the formula I (n=1) with particularly photostable properties are those where the substituents $R^1$ to $R^4$ are present in the combination stated in Table 1:

TABLE 1

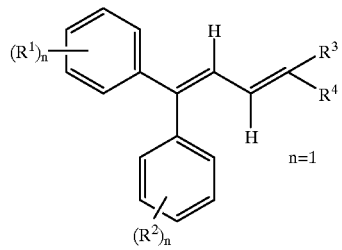

| $R^1$ | $R^2$ | Position | $R^3$ | $R^4$ |
|---|---|---|---|---|
| H | H | | H | $COR^6$ |
| H | H | | H | $CONR^5R^6$ |
| H | H | | H | CN |
| H | H | | $COOR^5$ | $COOR^6$ |
| H | H | | $COOR^5$ | $COR^6$ |
| H | H | | $COR^5$ | $COR^6$ |
| H | H | | $CONR^5R^6$ | $COOR^6$ |
| H | H | | $CONR^5R^6$ | $COR^6$ |
| H | H | | $CONR^5R^6$ | $CONR^5R^6$ |
| H | H | | CN | $COR^6$ |
| H | H | | CN | $CONR^5R^6$ |
| H | H | | CN | CN |
| $C_1$—$C_8$-Alkoxy | $C_1$—$C_8$-Alkoxy | para | H | $COR^6$ |
| $C_1$—$C_8$-Alkoxy | $C_1$—$C_8$-Alkoxy | ortho | H | $COR^6$ |
| $C_1$—$C_8$-Alkoxy | $C_1$—$C_8$-Alkoxy | meta | H | $COR^6$ |
| $C_1$—$C_8$-Alkoxy | $C_1$—$C_8$-Alkoxy | para | H | $CONR^5R^6$ |
| $C_1$—$C_8$-Alkoxy | $C_1$—$C_8$-Alkoxy | ortho | H | $CONR^5R^6$ |
| $C_1$—$C_8$-Alkoxy | $C_1$—$C_8$-Alkoxy | meta | H | $CONR^5R^6$ |
| $C_1$—$C_8$-Alkoxy | $C_1$—$C_8$-Alkoxy | para | H | CN |
| $C_1$—$C_8$-Alkoxy | $C_1$—$C_8$-Alkoxy | ortho | H | CN |
| $C_1$—$C_8$-Alkoxy | $C_1$—$C_8$-Alkoxy | meta | H | CN |
| $C_1$—$C_8$-Alkoxy | $C_1$—$C_8$-Alkoxy | para | $COOR^5$ | $COOR^6$ |
| $C_1$—$C_8$-Alkoxy | $C_1$—$C_8$-Alkoxy | ortho | $COOR^5$ | $COOR^6$ |
| $C_1$—$C_8$-Alkoxy | $C_1$—$C_8$-Alkoxy | meta | $COOR^5$ | $COOR^6$ |
| $C_1$—$C_8$-Alkoxy | $C_1$—$C_8$-Alkoxy | para | $COOR^5$ | $COR^6$ |
| $C_1$—$C_8$-Alkoxy | $C_1$—$C_8$-Alkoxy | ortho | $COOR^5$ | $COR^6$ |
| $C_1$—$C_8$-Alkoxy | $C_1$—$C_8$-Alkoxy | meta | $COOR^5$ | $COR^6$ |
| $C_1$—$C_8$-Alkoxy | $C_1$—$C_8$-Alkoxy | para | $COR^5$ | $COR^6$ |
| $C_1$—$C_8$-Alkoxy | $C_1$—$C_8$-Alkoxy | ortho | $COR^5$ | $COR^6$ |
| $C_1$—$C_8$-Alkoxy | $C_1$—$C_8$-Alkoxy | meta | $COR^5$ | $COR^6$ |
| $C_1$—$C_8$-Alkoxy | $C_1$—$C_8$-Alkoxy | para | $CONR^5R^6$ | $COOR^6$ |
| $C_1$—$C_8$-Alkoxy | $C_1$—$C_8$-Alkoxy | ortho | $CONR^5R^6$ | $COOR^6$ |
| $C_1$—$C_8$-Alkoxy | $C_1$—$C_8$-Alkoxy | meta | $CONR^5R^6$ | $COOR^6$ |
| $C_1$—$C_8$-Alkoxy | $C_1$—$C_8$-Alkoxy | para | $CONR^5R^6$ | $COR^6$ |
| $C_1$—$C_8$-Alkoxy | $C_1$—$C_8$-Alkoxy | ortho | $CONR^5R^6$ | $COR^6$ |
| $C_1$—$C_8$-Alkoxy | $C_1$—$C_8$-Alkoxy | meta | $CONR^5R^6$ | $COR^6$ |
| $C_1$—$C_8$-Alkoxy | $C_1$—$C_8$-Alkoxy | para | $CONR^5R^6$ | $CONR^5R^6$ |
| $C_1$—$C_8$-Alkoxy | $C_1$—$C_8$-Alkoxy | ortho | $CONR^5R^6$ | $CONR^5R^6$ |
| $C_1$—$C_8$-Alkoxy | $C_1$—$C_8$-Alkoxy | meta | $CONR^5R^6$ | $CONR^5R^6$ |
| $C_1$—$C_8$-Alkoxy | $C_1$—$C_8$-Alkoxy | para | CN | $COR^6$ |
| $C_1$—$C_8$-Alkoxy | $C_1$—$C_8$-Alkoxy | ortho | CN | $COR^6$ |
| $C_1$—$C_8$-Alkoxy | $C_1$—$C_8$-Alkoxy | meta | CN | $COR^6$ |
| $C_1$—$C_8$-Alkoxy | $C_1$—$C_8$-Alkoxy | para | CN | $CONR^5R^6$ |
| $C_1$—$C_8$-Alkoxy | $C_1$—$C_8$-Alkoxy | ortho | CN | $CONR^5R^6$ |
| $C_1$—$C_8$-Alkoxy | $C_1$—$C_8$-Alkoxy | meta | CN | $CONR^5R^6$ |
| $C_1$—$C_8$-Alkoxy | $C_1$—$C_8$-Alkoxy | para | CN | CN |
| $C_1$—$C_8$-Alkoxy | $C_1$—$C_8$-Alkoxy | ortho | CN | CN |
| $C_1$—$C_8$-Alkoxy | $C_1$—$C_8$-Alkoxy | meta | CN | CN |
| $C_1$—$C_{12}$-Alkoxy | $C_1$—$C_{12}$-Alkoxy | para | H | $COR^6$ |
| $C_1$—$C_{12}$-Alkoxy | $C_1$—$C_{12}$-Alkoxy | ortho | H | $COR^6$ |
| $C_1$—$C_{12}$-Alkoxy | $C_1$—$C_{12}$-Alkoxy | meta | H | $COR^6$ |
| $C_1$—$C_{12}$-Alkoxy | $C_1$—$C_{12}$-Alkoxy | para | H | $CONR^5R^6$ |
| $C_1$—$C_{12}$-Alkoxy | $C_1$—$C_{12}$-Alkoxy | ortho | H | $CONR^5R^6$ |
| $C_1$—$C_{12}$-Alkoxy | $C_1$—$C_{12}$-Alkoxy | meta | H | $CONR^5R^6$ |
| $C_1$—$C_{12}$-Alkoxy | $C_1$—$C_{12}$-Alkoxy | para | H | CN |
| $C_1$—$C_{12}$-Alkoxy | $C_1$—$C_{12}$-Alkoxy | ortho | H | CN |
| $C_1$—$C_{12}$-Alkoxy | $C_1$—$C_{12}$-Alkoxy | meta | H | CN |
| $C_1$—$C_{12}$-Alkoxy | $C_1$—$C_{12}$-Alkoxy | para | $COOR^5$ | $COOR^6$ |
| $C_1$—$C_{12}$-Alkoxy | $C_1$—$C_{12}$-Alkoxy | ortho | $COOR^5$ | $COOR^6$ |
| $C_1$—$C_{12}$-Alkoxy | $C_1$—$C_{12}$-Alkoxy | meta | $COOR^5$ | $COOR^6$ |
| $C_1$—$C_{12}$-Alkoxy | $C_1$—$C_{12}$-Alkoxy | para | $COOR^5$ | $COR^6$ |
| $C_1$—$C_{12}$-Alkoxy | $C_1$—$C_{12}$-Alkoxy | ortho | $COOR^5$ | $COR^6$ |
| $C_1$—$C_{12}$-Alkoxy | $C_1$—$C_{12}$-Alkoxy | meta | $COOR^5$ | $COR^6$ |
| $C_1$—$C_{12}$-Alkoxy | $C_1$—$C_{12}$-Alkoxy | para | $COR^5$ | $COR^6$ |
| $C_1$—$C_{12}$-Alkoxy | $C_1$—$C_{12}$-Alkoxy | ortho | $COR^5$ | $COR^6$ |
| $C_1$—$C_{12}$-Alkoxy | $C_1$—$C_{12}$-Alkoxy | meta | $COR^5$ | $COR^6$ |
| $C_1$—$C_{12}$-Alkoxy | $C_1$—$C_{12}$-Alkoxy | para | $CONR^5R^6$ | $COOR^6$ |
| $C_1$—$C_{12}$-Alkoxy | $C_1$—$C_{12}$-Alkoxy | ortho | $CONR^5R^6$ | $COOR^6$ |
| $C_1$—$C_{12}$-Alkoxy | $C_1$—$C_{12}$-Alkoxy | meta | $CONR^5R^6$ | $COOR^6$ |
| $C_1$—$C_{12}$-Alkoxy | $C_1$—$C_{12}$-Alkoxy | para | $CONR^5R^6$ | $COR^6$ |
| $C_1$—$C_{12}$-Alkoxy | $C_1$—$C_{12}$-Alkoxy | ortho | $CONR^5R^6$ | $COR^6$ |
| $C_1$—$C_{12}$-Alkoxy | $C_1$—$C_{12}$-Alkoxy | meta | $CONR^5R^6$ | $COR^6$ |
| $C_1$—$C_{12}$-Alkoxy | $C_1$—$C_{12}$-Alkoxy | para | $CONR^5R^6$ | $CONR^5R^6$ |
| $C_1$—$C_{12}$-Alkoxy | $C_1$—$C_{12}$-Alkoxy | ortho | $CONR^5R^6$ | $CONR^5R^6$ |
| $C_1$—$C_{12}$-Alkoxy | $C_1$—$C_{12}$-Alkoxy | meta | $CONR^5R^6$ | $CONR^5R^6$ |
| $C_1$—$C_{12}$-Alkoxy | $C_1$—$C_{12}$-Alkoxy | para | CN | $COR^6$ |
| $C_1$—$C_{12}$-Alkoxy | $C_1$—$C_{12}$-Alkoxy | ortho | CN | $COR^6$ |
| $C_1$—$C_{12}$-Alkoxy | $C_1$—$C_{12}$-Alkoxy | meta | CN | $COR^6$ |
| $C_1$—$C_{12}$-Alkoxy | $C_1$—$C_{12}$-Alkoxy | para | CN | $CONR^5R^6$ |
| $C_1$—$C_{12}$-Alkoxy | $C_1$—$C_{12}$-Alkoxy | ortho | CN | $CONR^5R^6$ |
| $C_1$—$C_{12}$-Alkoxy | $C_1$—$C_{12}$-Alkoxy | meta | CN | $CONR^5R^6$ |
| $C_1$—$C_{12}$-Alkoxy | $C_1$—$C_{12}$-Alkoxy | para | CN | CN |
| $C_1$—$C_{12}$-Alkoxy | $C_1$—$C_{12}$-Alkoxy | ortho | CN | CN |
| $C_1$—$C_{12}$-Alkoxy | $C_1$—$C_{12}$-Alkoxy | meta | CN | CN |
| Carboxylate | Carboxylate | para | H | $COR^6$ |
| Carboxylate | Carboxylate | ortho | H | $COR^6$ |
| Carboxylate | Carboxylate | meta | H | $COR^6$ |
| Carboxylate | Carboxylate | para | H | $CONR^5R^6$ |
| Carboxylate | Carboxylate | ortho | H | $CONR^5R^6$ |
| Carboxylate | Carboxylate | meta | H | $CONR^5R^6$ |

TABLE 1-continued

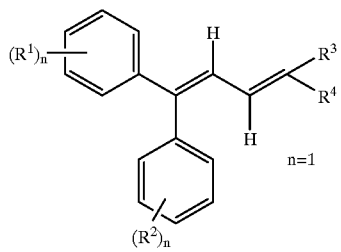

n=1

| R¹ | R² | Position | R³ | R⁴ |
|---|---|---|---|---|
| Carboxylate | Carboxylate | para | H | CN |
| Carboxylate | Carboxylate | ortho | H | CN |
| Carboxylate | Carboxylate | meta | H | CN |
| Carboxylate | Carboxylate | para | COOR⁵ | COOR⁶ |
| Carboxylate | Carboxylate | ortho | COOR⁵ | COOR⁶ |
| Carboxylate | Carboxylate | meta | COOR⁵ | COOR⁶ |
| Carboxylate | Carboxylate | para | COOR⁵ | COR⁶ |
| Carboxylate | Carboxylate | ortho | COOR⁵ | COR⁶ |
| Carboxylate | Carboxylate | meta | COOR⁵ | COR⁶ |
| Carboxylate | Carboxylate | para | COR⁵ | COR⁶ |
| Carboxylate | Carboxylate | ortho | COR⁵ | COR⁶ |
| Carboxylate | Carboxylate | meta | COR⁵ | COR⁶ |
| Carboxylate | Carboxylate | para | CONR⁵R⁶ | COOR⁶ |
| Carboxylate | Carboxylate | ortho | CONR⁵R⁶ | COOR⁶ |
| Carboxylate | Carboxylate | meta | CONR⁵R⁶ | COOR⁶ |
| Carboxylate | Carboxylate | para | CONR⁵R⁶ | COR⁶ |
| Carboxylate | Carboxylate | ortho | CONR⁵R⁶ | COR⁶ |
| Carboxylate | Carboxylate | meta | CONR⁵R⁶ | COR⁶ |
| Carboxylate | Carboxylate | para | CONR⁵R⁶ | CONR⁵R⁶ |
| Carboxylate | Carboxylate | ortho | CONR⁵R⁶ | CONR⁵R⁶ |
| Carboxylate | Carboxylate | meta | CONR⁵R⁶ | CONR⁵R⁶ |
| Carboxylate | Carboxylate | para | CN | COR⁶ |
| Carboxylate | Carboxylate | ortho | CN | COR⁶ |
| Carboxylate | Carboxylate | meta | CN | COR⁶ |
| Carboxylate | Carboxylate | para | CN | CONR⁵R⁶ |
| Carboxylate | Carboxylate | ortho | CN | CONR⁵R⁶ |
| Carboxylate | Carboxylate | meta | CN | CONR⁵R⁶ |
| Carboxylate | Carboxylate | para | CN | CN |
| Carboxylate | Carboxylate | ortho | CN | CN |
| Carboxylate | Carboxylate | meta | CN | CN |
| Sulfonate | Sulfonate | para | H | COR⁶ |
| Sulfonate | Sulfonate | ortho | H | COR⁶ |
| Sulfonate | Sulfonate | meta | H | COR⁶ |
| Sulfonate | Sulfonate | para | H | CONR⁵R⁶ |
| Sulfonate | Sulfonate | ortho | H | CONR⁵R⁶ |
| Sulfonate | Sulfonate | meta | H | CONR⁵R⁶ |
| Sulfonate | Sulfonate | para | H | CN |
| Sulfonate | Sulfonate | ortho | H | CN |
| Sulfonate | Sulfonate | meta | H | CN |
| Sulfonate | Sulfonate | para | COOR⁵ | COOR⁶ |
| Sulfonate | Sulfonate | ortho | COOR⁵ | COOR⁶ |
| Sulfonate | Sulfonate | meta | COOR⁵ | COOR⁶ |
| Sulfonate | Sulfonate | para | COOR⁵ | COR⁶ |
| Sulfonate | Sulfonate | ortho | COOR⁵ | COR⁶ |
| Sulfonate | Sulfonate | meta | COOR⁵ | COR⁶ |
| Sulfonate | Sulfonate | para | COR⁵ | COR⁶ |
| Sulfonate | Sulfonate | ortho | COR⁵ | COR⁶ |
| Sulfonate | Sulfonate | meta | COR⁵ | COR⁶ |
| Sulfonate | Sulfonate | para | CONR⁵R⁶ | COOR⁶ |
| Sulfonate | Sulfonate | ortho | CONR⁵R⁶ | COOR⁶ |
| Sulfonate | Sulfonate | meta | CONR⁵R⁶ | COOR⁶ |
| Sulfonate | Sulfonate | para | CONR⁵R⁶ | COR⁶ |
| Sulfonate | Sulfonate | ortho | CONR⁵R⁶ | COR⁶ |
| Sulfonate | Sulfonate | meta | CONR⁵R⁶ | COR⁶ |
| Sulfonate | Sulfonate | para | CONR⁵R⁶ | CONR⁵R⁶ |
| Sulfonate | Sulfonate | ortho | CONR⁵R⁶ | CONR⁵R⁶ |
| Sulfonate | Sulfonate | meta | CONR⁵R⁶ | CONR⁵R⁶ |
| Sulfonate | Sulfonate | para | CN | COR⁶ |
| Sulfonate | Sulfonate | ortho | CN | COR⁶ |
| Sulfonate | Sulfonate | meta | CN | COR⁶ |
| Sulfonate | Sulfonate | para | CN | CONR⁵R⁶ |
| Sulfonate | Sulfonate | ortho | CN | CONR⁵R⁶ |
| Sulfonate | Sulfonate | meta | CN | CONR⁵R⁶ |
| Sulfonate | Sulfonate | para | CN | CN |

TABLE 1-continued

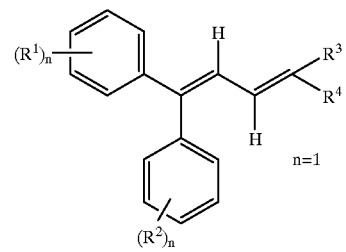

n=1

| R¹ | R² | Position | R³ | R⁴ |
|---|---|---|---|---|
| Sulfonate | Sulfonate | ortho | CN | CN |
| Sulfonate | Sulfonate | meta | CN | CN |
| Ammonium | Ammonium | para | H | COR⁶ |
| Ammonium | Ammonium | ortho | H | COR⁶ |
| Ammonium | Ammonium | meta | H | COR⁶ |
| Ammonium | Ammonium | para | H | CONR⁵R⁶ |
| Ammonium | Ammonium | ortho | H | CONR⁵R⁶ |
| Ammonium | Ammonium | meta | H | CONR⁵R⁶ |
| Ammonium | Ammonium | para | H | CN |
| Ammonium | Ammonium | ortho | H | CN |
| Ammonium | Ammonium | meta | H | CN |
| Ammonium | Ammonium | para | COOR⁵ | COOR⁶ |
| Ammonium | Ammonium | ortho | COOR⁵ | COOR⁶ |
| Ammonium | Ammonium | meta | COOR⁵ | COOR⁶ |
| Ammonium | Ammonium | para | COOR⁵ | COR⁶ |
| Ammonium | Ammonium | ortho | COOR⁵ | COR⁶ |
| Ammonium | Ammonium | meta | COOR⁵ | COR⁶ |
| Ammonium | Ammonium | para | COR⁵ | COR⁶ |
| Ammonium | Ammonium | ortho | COR⁵ | COR⁶ |
| Ammonium | Ammonium | meta | COR⁵ | COR⁶ |
| Ammonium | Ammonium | para | CONR⁵R⁶ | COOR⁶ |
| Ammonium | Ammonium | ortho | CONR⁵R⁶ | COOR⁶ |
| Ammonium | Ammonium | meta | CONR⁵R⁶ | COOR⁶ |
| Ammonium | Ammonium | para | CONR⁵R⁶ | COR⁶ |
| Ammonium | Ammonium | ortho | CONR⁵R⁶ | COR⁶ |
| Ammonium | Ammonium | meta | CONR⁵R⁶ | COR⁶ |
| Ammonium | Ammonium | para | CONR⁵R⁶ | CONR⁵R⁶ |
| Ammonium | Ammonium | ortho | CONR⁵R⁶ | CONR⁵R⁶ |
| Ammonium | Ammonium | meta | CONR⁵R⁶ | CONR⁵R⁶ |
| Ammonium | Ammonium | para | CN | COR⁶ |
| Ammonium | Ammonium | ortho | CN | COR⁶ |
| Ammonium | Ammonium | meta | CN | COR⁶ |
| Ammonium | Ammonium | para | CN | CONR⁵R⁶ |
| Ammonium | Ammonium | ortho | CN | CONR⁵R⁶ |
| Ammonium | Ammonium | meta | CN | CONR⁵R⁶ |
| Ammonium | Ammonium | para | CN | CN |
| Ammonium | Ammonium | ortho | CN | CN |
| Ammonium | Ammonium | meta | CN | CN |

Likewise very particularly preferred is the use of those compounds of the formula I where $R^1$ and $R^2$ are independently of one another hydrogen, $C_1$–$C_{12}$-alkyl, $C_1$–$C_8$-alkoxy,
  substituents which confer solubility in water and are selected from the group consisting of carboxylate, sulfonate or ammonium residues;

$R^3$ is $COOR^5$, $COR^5$, $CONR^5R^6$;

$R^4$ is $COOR^6$, $COR^6$, $CONR^5R^6$;

$R^5$ and $R^6$ are independently of one another hydrogen, $C_1$–$C_{12}$-alkyl, $C_3$–$C_6$-cycloalkyl, $C_7$–$C_{10}$-bicycloalkyl, phenyl, naphthyl, unsubstituted or substituted;

n is from 1 to 3, since these compounds are particularly photostable and, at the same time, colorless.

The invention also relates to 4,4-diarylbutadienes of the formula Ia,

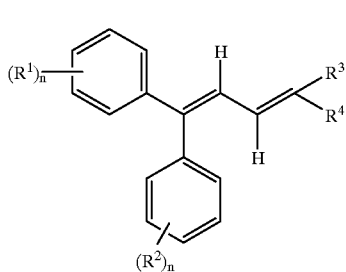

Ia where the diene system has the Z,Z; Z,E; E,Z or E,E configuration or a mixture thereof, and where the variables independently of one another have the following meanings:

$R^1$ and $R^2$ hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, unsubstituted or substituted, substituents which confer solubility in water and are selected from the group consisting of carboxylate, sulfonate or ammonium residues;

$R^3$ $COOR^5$, $CONR^5R^6$;

$R^4$ $COOR^6$, $CONR^5R^6$;

$R^5$ and $R^6$ hydrogen, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted;

n 1 to 3, where $R^3$ and $R^4$ may not be $COOCH_3$ when $R^1$ and $R^2$ are hydrogen.

Preferred 4,4-diarylbutadienes are those of the formula Ib,

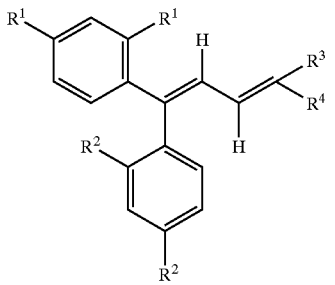

Ib where the diene system has the Z,Z; Z,E; E,Z or E,E configuration or a mixture thereof, and where the variables independently of one another have the following meanings:

$R^1$ and $R^2$ hydrogen, $C_1$–$C_{20}$-alkyl, $C_1$–$C_{12}$-alkoxy, $C_1$–$C_{20}$-alkoxycarbonyl;

$R^3$ $COOR^5$, $CONR^5R^6$;

$R^4$ $COOR^6$, $CONR^5R^6$;

$R^5$ and $R^6$ hydrogen, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted;

where $R^3$ and $R^4$ may not be $COOCH_3$ when $R^1$ and $R^2$ are hydrogen.

Particularly preferred 4,4-diarylbutadienes are those of the formula Ic,

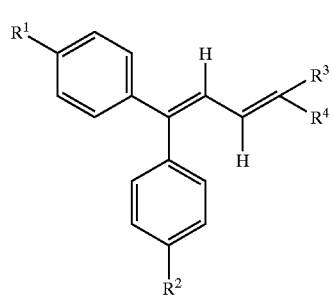

Ic where the diene system has the Z,Z; Z,E; E,Z or E,E configuration or a mixture htereof, and where the variables independently of one another have the following meanings:

$R^1$ and $R^2$ hydrogen, $C_1$–$C_{20}$-alkyl, $C_1$–$C_{12}$-alkoxy, $C_1$–$C_{20}$-alkoxycarbonyl;

$R^3$ $COOR^5$, $CONR^5R^6$;

$R^4$ $COOR^6$, $CONR^5R^6$;

$R^5$ and $R^6$ hydrogen, $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, hetaryl, unsubstituted or substituted;

where $R^3$ and $R^4$ may not be $COOCH_3$ when $R^1$ and $R^2$ are hydrogen.

The more accurate definition of the substituents $R^1$ to $R^6$ of compounds Ia to Ic corresponds to the description of compound I previously given in the introduction.

The compounds of the formula I to be used according to the invention can be prepared by condensation in accordance with the equation

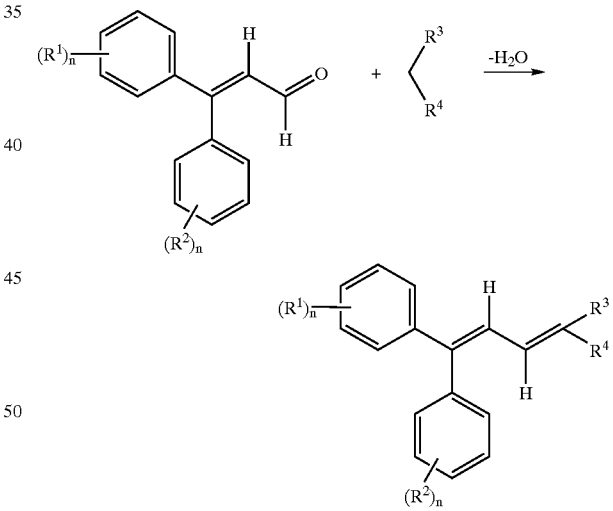

I where $R^1$ to $R^4$ have the meanings stated in claim 1.

The abovementioned condensation can be either base- or acid-catalyzed. Suitable catalysts are:

tertiary amines such as, for example, pyridine, morpholine, triethylamine, triethanolamine;

seconday amines such as, for example, piperidine, dimethylamine, diethylamine;

$NH_3$, $NaNH_2$, $KNH_2$, $NH_4OAc$;

basic alumina, basic ion exchangers;

$Na_2CO_3$, $K_2CO_3$;

acid catalysts such as, for example, glacial acetic acid, formic acid, propionic acid;

HCl, $H_2SO_4$, $HNO_3$;

acid ion exchangers.

The amount of the catalysts is in general 0.1 to 50 mol %, preferably 0.5 to 20 mol %, of the amount of aldehyde employed.

The temperatures preferably employed are from 20 to 150° C., in particular 30 to 100° C., particularly preferably from 40 to 80° C. No special conditions regarding the pressure are necessary; the reaction is generally carried out under atmospheric pressure.

Solvents which can be employed are alcohols such as, for example, methanol, ethanol or isopropanol; aromatic compounds such as, for example, toluene or xylene; hydrocarbons, for example heptane or hexane; chlorinated hydrocarbons such as, for example, chloroform or dichloromethane; miglyol, tetrahydrofuran. However, the reaction can also be carried out without solvent.

For example, reaction of β-phenylcinnamaldehyde with diethyl malonate in the presence of piperidine as catalyst affords compound 1 in Tab. 2.

It is also possible to prepare longer-chain esters starting from methyl or ethyl esters, such as, for example, compound 1 in Table 2, by transesterification reactions in the presence of a basic catalyst.

Catalysts suitable for the transesterification are:

basic alkali metal and alkaline earth metal salts, preferably those which are soluble neither in the precursors nor in the products and which can easily be removed after the end of the reaction, particularly preferably: sodium, potassium or calcium carbonate or sodium bicarbonate;

alkaline earth metal oxides, preferably calcium or magnesium oxide and basic zeolites.

The amount of the catalysts is generally from 1 to 80 mol %, preferably 5 to 50 mol %, of the amount of ester employed.

The amount of alcohol employed must be at least equimolar with the amount of initial ester employed, for example compound 1 in Table 2. Amounts of from 200 to 500 mol % of the alcohol are preferably employed.

The methanol or ethanol which is formed is removed by distillation.

The temperatures preferably employed are from 50 to 250° C., in particular 60 to 150° C. No special conditions regarding the pressure are necessary; the reaction is generally carried out under atmospheric pressure.

Solvents which can be employed are inert high-boiling compounds such as xylenes, but also toluene or mixtures of the alcohols employed with liquid, short-chain alkanes such as hexane and heptane. It is preferred to use no solvent except the alcohol employed.

The transesterification can be carried out either batchwise or continuously. In the continuous procedure, the reactants are preferably passed over a fixed bed of an insoluble base.

In the case where $R^3 \neq R^4$, the compounds of the formula I according to the invention can, in principle, be in the form of their various geometric isomers, i.e. with a diene system having the Z,Z; Z,E; E,Z and/or E,E configuration. The preferred cosmetic sunscreens are the all-E and/or all-Z isomers, very particularly preferably the all-E isomers.

If $R^3=R^4$, the C—C double bond between C-3 and C-4 (adjacent to the diaryl system) can have the E and/or Z configuration, preferably the Z configuration.

The present invention also relates to cosmetic and pharmaceutical preparations which comprise from 0.1 to 10% by weight, preferably 1 to 7% by weight, based on the total amount of the cosmetic and pharmaceutical preparation, of one or more of the compounds of the formula I together with compounds known per se for cosmetic and pharmaceutical preparations and absorbing in the UV-A and UV-B regions as sunscreens, generally employing the compounds of the formula I in a smaller amount than the UV-B-absorbing compounds.

The sunscreen-containing cosmetic and pharmaceutical preparations are, as a rule, based on a carrier which contains at least one oil phase. However, preparations with an exclusively aqueous basis are also possible on use of compounds having hydrophilic substituents. Accordingly, oils, oil-in-water and water-in-oil emulsions, creams and pastes, protective lipstick bases or non-greasy gels are suitable.

Sunscreen products of these types can accordingly be in liquid, pasty or solid form, for example as water-in-oil creams, oil-in-water creams and lotions, aerosol foam creams, gels, oils, grease sticks, dusting powders, sprays or hydroalcoholic lotions.

Examples of conventional cosmetic oil components are liquid paraffin, glyceryl stearate, isopropyl myristate, diisopropyl adipate, cetylstearyl 2-ethylhexanoate, hydrogenated polyisobutene, petrolatum, caprylic acid/capric acid triglycerides, microcrystalline wax, lanolin and stearic acid.

Conventional cosmetic ancillary substances which may be suitable as additives are, for example, coemulsifiers, fats and waxes, stabilizers, thickeners, biogenic active substances, film formers, fragrances, dyes, pearlescent agents, preservatives, pigments, electrolytes (eg. magnesium sulfate) and pH regulators. Suitable and preferred coemulsifiers are known water in oil (W/O) as well as oil in water (O/W) emulsifiers such as polyglycerol esters, sorbitan esters or partially esterified glycerides. Typical examples of fats are glycerides; waxes which may be mentioned are, inter alia, beeswax, paraffin wax or microwaxes, possibly combined with hydrophilic waxes. Stabilizers which can be employed are metal salts of fatty acids such as magnesium, aluminum and/or zinc stearate. Examples of suitable thickeners are crosslinked polyacrylic acids and their derivatives, polysaccharides, in particular xanthan gum, guar—guar, agar—agar, alginates and Tyloses, carboxymethylcellulose and hydroxyethylcellulose, also fatty alcohols, monoglycerides and fatty acids, polyacrylates, polyvinyl alcohol and polyvinylpyrrolidone. Examples of biogenic active substances are plant extracts, protein hydrolysates and vitamin complexes. Examples of film formers which are in use are hydrocolloids such as chitosan, microcrystalline chitosan or quaternized chitosan, polyvinylpyrrolidone, vinylpyrrolidone/vinyl acetate copolymers, polymers of the acrylic acid series, quaternary cellulose derivatives and similar compounds. Examples of suitable preservatives are formaldehyde solution, p-hydroxybenzoate or sorbic acid. Examples of suitable pearlescent agents are glycol distearic esters such as ethylene glycol distearate, but also fatty acids and fatty acid monoglycol esters. Dyes which can be used are the substances suitable and approved for cosmetic purposes, as tabulated, for example, in the publication "Kosmetische Färbemittel" of the Farbstoffkomission der Deutschen Forschungsgemeinschaft, published in Verlag Chemie, Weinheim, 1984. These dyes are normally employed in a concentration of from 0.001 to 0.1% of the total weight of the mixture.

The total content of ancillary substances and additives can be from 1 to 80, preferably 6 to 40, % by weight, and the nonaqueous content ("active substance") can be from 20 to 80, preferably 30 to 70, % by weight, based on the compositions. The compositions can be produced in a manner known per se, ie. for example by hot, cold, hot—hot/cold or Phase Inversion Temperature (PIT) emulsification. This is a purely mechanical process; no chemical reaction takes place.

Finally, it is also possible to use other substances which absorb in the UV region and are known per se as long as they are stable in the complete system of the combination of UV filters to be used according to the invention.

Most of the sunscreens in the cosmetic and pharmaceutical preparations used for protecting the human epidermis consist of compounds which absorb UV light in the UV-B region, ie. in the region from 280 to 320 nm. The content of UV-A absorbers to be used according to the invention is, for example, from 10 to 90%, preferably 20 to 50%, of the total weight of UV-B and UV-A absorbing substances.

Any V-A and UV-B filter substances are suitable as UV filter substances which are used in combination with the compounds of the formula I to be used according to the invention. Examples which may be mentioned are:

| No. | Substance | CAS No. (= acid) |
|---|---|---|
| 1 | 4-Aminobenzoic acid | 150-13-0 |
| 2 | 3-(4-Trimethylammonio)benzylidenebornan-2-one methyl sulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-dimethyl-2-oxobicyclo[2.2.1]heptane-1-methane-sulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4-Methylbenzylidene)bornan-2-one | 36861-47-9 |
| 14 | 3-Benzylidenebornan-2-one | 15087-24-8 |
| 15 | 1-(4-Isopropylphenyl)-3-phenylpropane-1,3-dione | 63250-25-9 |
| 16 | 4-Isopropylbenzyl salicylate | 94134-93-7 |
| 17 | 2,4,6-Tri(o-2-ethylhexoxycarbonyl-anilino)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2-Ethylhexyl 2-cyano-3,3-diphenylacrylate | 6197-30-4 |
| 21 | Menthyl o-aminobenzoate or: 5-methyl-2-(1-methylethyl)cyclohexyl 2-aminobenzoate | 134-09-8 |
| 22 | Glyceryl p-aminobenzoate or: 4-aminobenzoic acid 1-glyceryl ester | 136-44-7 |
| 23 | 2,2'-Dihydroxy-4-methoxybenzophenone (dioxybenzone) | 131-53-3 |
| 24 | 2-Hydroxy-4-methoxy-4'-methylbenzophenone (mexenone) | 1641-17-4 |
| 25 | Triethanolamine salicylate | 2174-16-5 |
| 26 | Dimethoxyphenylglyoxylic acid or: sodium 3,4-dimethoxyphenylglyoxylate | 4732-70-1 |
| 27 | 3-(4-Sulfobenzylidene)bornan-2-one and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

Finally, mention may also be made of micronized pigments such as titanium dioxide and zinc oxide.

To protect human hair from UV rays, the sunscreens of the formula I according to the invention can be incorporated into shampoos, lotions, gels, hair sprays, aerosol foam creams or emulsions in concentrations of from 0.1 to 10% by weight, preferably 1 to 7% by weight. The particular formulations can be used inter alia for washing, coloring and setting the hair.

The compounds to be used according to the invention as a rule have a particularly high absorbance in the region of UV-A radiation with a sharp band structure. They are furthermore readily soluble in cosmetic oils and can easily be incorporated into cosmetic formulations. Emulsions prepared using the compounds I show particularly high stability, the compounds I themselves show high photostability, and the preparations produced with I have a pleasant skin feel.

The UV filter action of the compounds of the formula I according to the invention can also be utilized for stabilizing active and ancillary substances in cosmetic and pharmaceutical formulations.

The invention also relates to the compounds of the formula I for use as medicine and to pharmaceutical compositions for preventive treatment of inflammations and allergies of the skin, and for preventing certain types of skin cancer, which comprise an effective amount of at least one compound of the formula I as active substance.

The pharmaceutical compositions according to the invention can be administered orally or topically. For oral administration, the pharmaceutical composition is in the form of, inter alia, pastilles, gelatine capsules, coated tablets, syrup, solution, emulsion or suspension. The pharmaceutical compositions are used topically for example as ointment, cream, gel, spray, solution or lotion.

EXAMPLES

I. Preparation

Example 1

Method for Preparing Compound No. 1 in Table 2

0.1 mol of β-phenylcinnamaldehyde and 0.1 mol of diethyl malonate were dissolved in 100 ml of methanol, 1 ml each of piperidine and glacial acetic acid was added, and the mixture was refluxed for 5 h. It is then diluted with water and cooled to 0° C., during which the final product crystallized out. The crystals were filtered off and dried to give 33 g (90% of theory) of compound 1 in Table 2 as colorless crystals. Purity: >99% (GC).

Compounds 2 and 3 and 8 to 15 in Table 2 are prepared as in Example 1.

Compounds 18 to 20 were prepared as in Example 1 by reacting diethyl malonate with the corresponding methyl-, tert-butyl- or methoxy-substituted β-phenylcinnamaldehydes.

Example 2

Compounds 4 to 7 in Table 2 were prepared by transesterification of the compound from Example 1 with the appropriate alcohols in the presence of sodium carbonate as catalyst. The liberated ethanol was distilled off, and the required products 4 to 7, which resulted as oil, were purified by distillation.

Example 3

Method for Preparing Compound No. 17 in Table 2

0.1 mol of camphor in 40 ml of xylene are mixed with 0.1 mol of KOH and heated to reflux. Then a solution of 0.105 mol of β-phenylcinnamaldehyde in xylene is slowly added dropwise over the course of 6 h. After cooling to room temperature, water is added, and the organic phase is washed twice with water and then dried over sodium sulfate. The oily residue after removal of the solvent is crystallized from methanol/water. 22 g (64%) of colorless crystals of compound 17 in Table 2 are obtained. Purity 99% (HPLC, isomer mixture).

Compound 16 in Table 2 is prepared by reacting β-phenylcinnamaldehyde with pinacolone as in Example 2.

TABLE 2

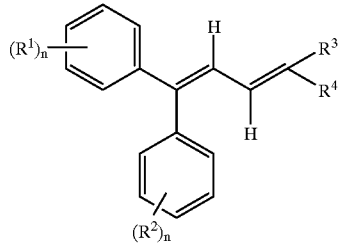

| No. | $\begin{array}{c}R^3\\R^4\end{array}$ | $R^1$ | $R^2$ | n | λmax (nm) | $E^1_1$ |
|---|---|---|---|---|---|---|
| 1) | 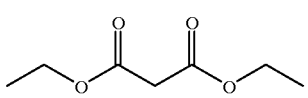 | H | H | 1 | 334 | 802 |
| 2) | 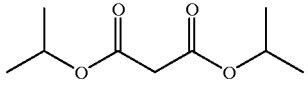 | H | H | 1 | 334 | 775 |
| 3) | 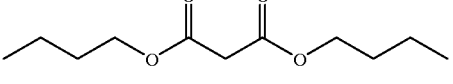 | H | H | 1 | 334 | 684 |
| 4) | 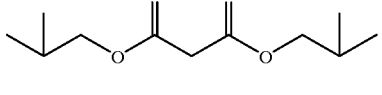 | H | H | 1 | 334 | 681 |
| 5) | 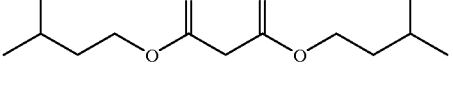 | H | H | 1 | 333 | 655 |
| 6) | 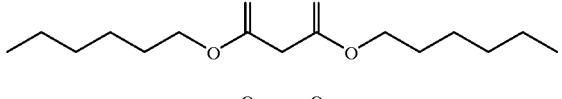 | H | H | 1 | 334 | 602 |
| 7) | 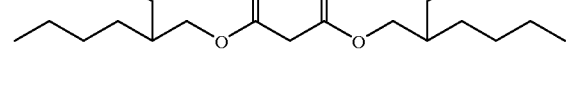 | H | H | 1 | 334 | 580 |
| 8) | 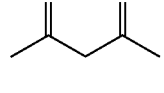 | H | H | 1 | 344 | 977 |
| 9) | 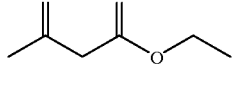 | H | H | 1 | 342 | 806 |
| 10) | 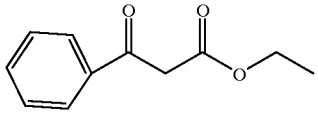 | H | H | 1 | 336 | 693 |

TABLE 2-continued
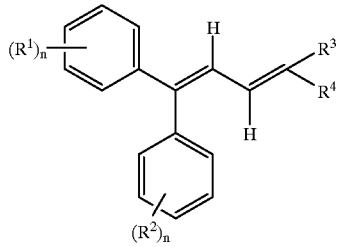
| No. | (R³,R⁴ group) | R¹ | R² | n | λmax (nm) | $E^1_1$ |
|---|---|---|---|---|---|---|
| 11) |  | H | H | 1 | 350 | 806 |
| 12) | 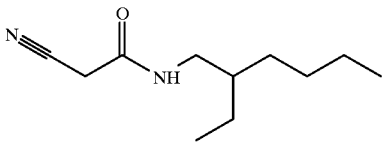 | H | H | 1 | 342 | 525 |
| 13) | 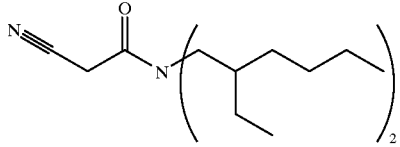 | H | H | 1 | 340 | 776 |
| 14) | 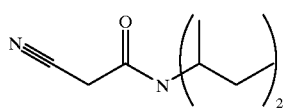 | H | H | 1 | 338 | 802 |
| 15) | 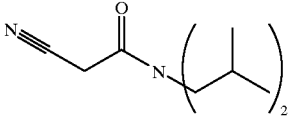 | H | H | 1 | 332 | 814 |
| 16) | 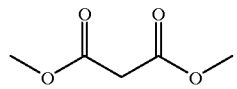 | H | H | 1 | 334 | 960 |
| 17) | 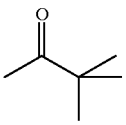 | H | H | 1 | 338 | 901 |
| 18) | 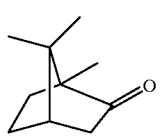 | 1) | 1) | 1 | 364 | 672 |
| 19) | 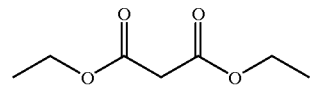 | 2) | 2) | 1 | 346 | 643 |

TABLE 2-continued

| No. | $\begin{array}{c}R^3\\R^4\end{array}$ | $R^1$ | $R^2$ | n | λmax (nm) | $E^1_1$ |
|---|---|---|---|---|---|---|
| 20) | diethyl malonate (ethyl ester O-C(=O)-CH₂-C(=O)-O-ethyl) | 3) | 3) | 2 | 338 | 699 |

1) $R^1=R^2$ = methoxy (substituted in the para position)
2) $R^1=R^2$ = tert-butyl (substituted in the para position)
3) $R^1=R^2$ = methyl (substituted in the ortho and para position)

The compounds in Tables 3 and 4 can be prepared in a similar way or as described in the general part.

TABLE 3

$R^5 = R^6$

| No. | $R^5=R^6$ | $R^1$ | $R^2$ | n | Position |
|---|---|---|---|---|---|
| 1) | n-Propyl | H | H | 1 | — |
| 2) | 2,2-Dimethylpropyl | H | H | 1 | — |
| 3) | n-Pentyl | H | H | 1 | — |
| 4) | 3-Methylbutyl | H | H | 1 | — |
| 5) | 2-Methylbutyl | H | H | 1 | — |
| 6) | 1-Methylbutyl | H | H | 1 | — |
| 7) | n-Heptyl | H | H | 1 | — |
| 8) | n-Octyl | H | H | 1 | — |
| 9) | Methyl | Methyl | Methyl | 1 | para |
| 10) | Ethyl | Methyl | Methyl | 1 | para |
| 11) | n-Propyl | Methyl | Methyl | 2 | para |
| 12) | iso-Propyl | Methyl | Methyl | 1 | para |
| 13) | n-Butyl | Methyl | Methyl | 1 | para |
| 14) | 2-Methylpropyl | Methyl | Methyl | 1 | para |
| 15) | 1-Methylpropyl | Methyl | Methyl | 1 | para |
| 16) | 2,2-Dimethylpropyl | Methyl | Methyl | 1 | para |
| 17) | n-Pentyl | Methyl | Methyl | 1 | para |
| 18) | 3-Methylbutyl | Methyl | Methyl | 1 | para |
| 19) | 2-Methylbutyl | Methyl | Methyl | 1 | para |
| 20) | 1-Methylbutyl | Methyl | Methyl | 2 | para |
| 21) | n-Hexyl | Methyl | Methyl | 1 | para |
| 22) | n-Heptyl | Methyl | Methyl | 1 | para |
| 23) | n-Octyl | Methyl | Methyl | 1 | para |
| 24) | 2-Ethylhexyl | Methyl | Methyl | 1 | para |
| 25) | Methyl | Ethyl | Ethyl | 1 | para |
| 26) | Ethyl | Ethyl | Ethyl | 1 | para |
| 27) | n-Propyl | Ethyl | Ethyl | 1 | para |
| 28) | iso-Propyl | Ethyl | Ethyl | 1 | para |
| 29) | n-Butyl | Ethyl | Ethyl | 1 | para |

TABLE 3-continued $R^5 = R^6$

| No. | $R^5=R^6$ | $R^1$ | $R^2$ | n | Position |
|---|---|---|---|---|---|
| 30) | 2-Methylpropyl | Ethyl | Ethyl | 1 | para |
| 31) | 1-Methylpropyl | Ethyl | Ethyl | 1 | para |
| 32) | 2,2-Dimethylpropyl | Ethyl | Ethyl | 1 | para |
| 33) | n-Pentyl | Ethyl | Ethyl | 1 | para |
| 34) | 3-Methylbutyl | Ethyl | Ethyl | 1 | para |
| 35) | 2-Methylbutyl | Ethyl | Ethyl | 1 | para |
| 36) | 1-Methylbutyl | Ethyl | Ethyl | 1 | para |
| 37) | n-Hexyl | Ethyl | Ethyl | 1 | para |
| 38) | n-Heptyl | Ethyl | Ethyl | 1 | para |
| 39) | n-Octyl | Ethyl | Ethyl | 1 | para |
| 40) | 2-Ethylhexyl | Ethyl | Ethyl | 1 | para |
| 41) | Methyl | n-Propyl | n-Propyl | 1 | para |
| 42) | Ethyl | n-Propyl | n-Propyl | 1 | para |
| 43) | n-Propyl | n-Propyl | n-Propyl | 1 | para |
| 44) | iso-Propyl | n-Propyl | n-Propyl | 1 | para |
| 45) | n-Butyl | n-Propyl | n-Propyl | 1 | para |
| 46) | 2-Methylpropyl | n-Propyl | n-Propyl | 1 | para |
| 47) | 1-Methylpropyl | n-Propyl | n-Propyl | 1 | para |
| 48) | 2,2-Dimethylpropyl | n-Propyl | n-Propyl | 1 | para |
| 49) | n-Pentyl | n-Propyl | n-Propyl | 1 | para |
| 50) | 3-Methylbutyl | n-Propyl | n-Propyl | 1 | para |
| 51) | 2-Methylbutyl | n-Propyl | n-Propyl | 1 | para |
| 52) | 1-Methylbutyl | n-Propyl | n-Propyl | 1 | para |
| 53) | n-Hexyl | n-Propyl | n-Propyl | 1 | para |
| 54) | n-Heptyl | n-Propyl | n-Propyl | 1 | para |
| 55) | n-Octyl | n-Propyl | n-Propyl | 1 | para |
| 56) | 2-Ethylhexyl | n-Propyl | n-Propyl | 1 | para |
| 57) | Methyl | i-Propyl | i-Propyl | 1 | para |
| 58) | Ethyl | i-Propyl | i-Propyl | 1 | para |
| 59) | n-Propyl | i-Propyl | i-Propyl | 1 | para |
| 60) | iso-Propyl | i-Propyl | i-Propyl | 1 | para |
| 61) | n-Butyl | i-Propyl | i-Propyl | 1 | para |

TABLE 3-continued

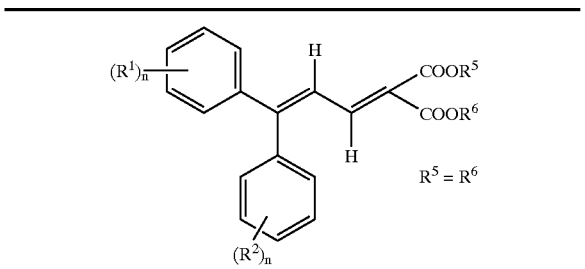

$R^5 = R^6$

TABLE 3-continued

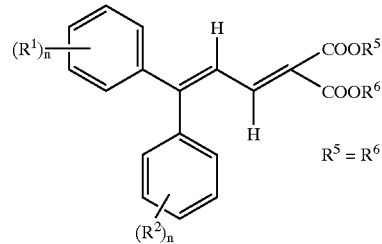

$R^5 = R^6$

| No. | $R^5=R^6$ | $R^1$ | $R^2$ | n | Position |
|---|---|---|---|---|---|
| 62) | 2-Methylpropyl | i-Propyl | i-Propyl | 1 | para |
| 63) | 1-Methylpropyl | i-Propyl | i-Propyl | 1 | para |
| 64) | 2,2-Dimethylpropyl | i-Propyl | i-Propyl | 1 | para |
| 65) | n-Pentyl | i-Propyl | i-Propyl | 1 | para |
| 66) | 3-Methylbutyl | i-Propyl | i-Propyl | 1 | para |
| 67) | 2-Methylbutyl | i-Propyl | i-Propyl | 1 | para |
| 68) | 1-Methylbutyl | i-Propyl | i-Propyl | 1 | para |
| 69) | n-Hexyl | i-Propyl | i-Propyl | 1 | para |
| 70) | n-Heptyl | i-Propyl | i-Propyl | 1 | para |
| 71) | n-Octyl | i-Propyl | i-Propyl | 1 | para |
| 72) | 2-Ethylhexyl | i-Propyl | i-Propyl | 1 | para |
| 73) | Methyl | n-Butyl | n-Butyl | 1 | para |
| 74) | Ethyl | n-Butyl | n-Butyl | 1 | para |
| 75) | n-Propyl | n-Butyl | n-Butyl | 1 | para |
| 76) | iso-Propyl | n-Butyl | n-Butyl | 1 | para |
| 77) | n-Butyl | n-Butyl | n-Butyl | 1 | para |
| 78) | 2-Methylpropyl | n-Butyl | n-Butyl | 1 | para |
| 79) | 1-Methylpropyl | n-Butyl | n-Butyl | 1 | para |
| 80) | 2,2-Dimethylpropyl | n-Butyl | n-Butyl | 1 | para |
| 81) | n-Pentyl | n-Butyl | n-Butyl | 1 | para |
| 82) | 3-Methylbutyl | n-Butyl | n-Butyl | 1 | para |
| 83) | 2-Methylbutyl | n-Butyl | n-Butyl | 1 | para |
| 84) | 1-Methylbutyl | n-Butyl | n-Butyl | 1 | para |
| 85) | n-Hexyl | n-Butyl | n-Butyl | 1 | para |
| 86) | n-Heptyl | n-Butyl | n-Butyl | 1 | para |
| 87) | n-Octyl | n-Butyl | n-Butyl | 1 | para |
| 88) | 2-Ethylhexyl | n-Butyl | n-Butyl | 1 | para |
| 89) | Methyl | 1-Methylpropyl | 1-Methylpropyl | 1 | para |
| 90) | Ethyl | 1-Methylpropyl | 1-Methylpropyl | 1 | para |
| 91) | n-Propyl | 1-Methylpropyl | 1-Methylpropyl | 1 | para |
| 92) | iso-Propyl | 1-Methylpropyl | 1-Methylpropyl | 1 | para |
| 93) | n-Butyl | 1-Methylpropyl | 1-Methylpropyl | 1 | para |
| 94) | 2-Methylpropyl | 1-Methylpropyl | 1-Methylpropyl | 1 | para |
| 95) | 1-Methylpropyl | 1-Methylpropyl | 1-Methylpropyl | 1 | para |
| 96) | 2,2-Dimethylpropyl | 1-Methylpropyl | 1-Methylpropyl | 1 | para |
| 97) | n-Pentyl | 1-Methylpropyl | 1-Methylpropyl | 1 | para |
| 98) | 3-Methylbutyl | 1-Methylpropyl | 1-Methylpropyl | 1 | para |
| 99) | 2-Methylbutyl | 1-Methylpropyl | 1-Methylpropyl | 1 | para |
| 100) | 1-Methylbutyl | 1-Methylpropyl | 1-Methylpropyl | 1 | para |
| 101) | n-Hexyl | 1-Methylpropyl | 1-Methylpropyl | 1 | para |
| 102) | n-Heptyl | 1-Methylpropyl | 1-Methylpropyl | 1 | para |
| 103) | n-Octyl | 1-Methylpropyl | 1-Methylpropyl | 1 | para |
| 104) | 2-Ethylhexyl | 1-Methylpropyl | 1-Methylpropyl | 1 | para |
| 105) | Methyl | 2-Methylpropyl | 2-Methylpropyl | 1 | para |
| 106) | Ethyl | 2-Methylpropyl | 2-Methylpropyl | 1 | para |
| 107) | n-Propyl | 2-Methylpropyl | 2-Methylpropyl | 1 | para |
| 108) | iso-Propyl | 2-Methylpropyl | 2-Methylpropyl | 1 | para |
| 109) | n-Butyl | 2-Methylpropyl | 2-Methylpropyl | 1 | para |
| 110) | 2-Methylpropyl | 2-Methylpropyl | 2-Methylpropyl | 1 | para |
| 111) | 1-Methylpropyl | 2-Methylpropyl | 2-Methylpropyl | 1 | para |
| 112) | 2,2-Dimethylpropyl | 2-Methylpropyl | 2-Methylpropyl | 1 | para |
| 113) | n-Pentyl | 2-Methylpropyl | 2-Methylpropyl | 1 | para |
| 114) | 3-Methylbutyl | 2-Methylpropyl | 2-Methylpropyl | 1 | para |
| 115) | 2-Methylbutyl | 2-Methylpropyl | 2-Methylpropyl | 1 | para |
| 116) | 1-Methylbutyl | 2-Methylpropyl | 2-Methylpropyl | 1 | para |
| 117) | n-Hexyl | 2-Methylpropyl | 2-Methylpropyl | 1 | para |
| 118) | n-Heptyl | 2-Methylpropyl | 2-Methylpropyl | 1 | para |
| 119) | n-Octyl | 2-Methylpropyl | 2-Methylpropyl | 1 | para |
| 120) | 2-Ethylhexyl | 2-Methylpropyl | 2-Methylpropyl | 1 | para |
| 121) | Methyl | n-Pentyl | n-Pentyl | 1 | para |
| 122) | Ethyl | n-Pentyl | n-Pentyl | 1 | para |
| 123) | n-Propyl | n-Pentyl | n-Pentyl | 1 | para |
| 124) | iso-Propyl | n-Pentyl | n-Pentyl | 1 | para |
| 125) | n-Butyl | n-Pentyl | n-Pentyl | 1 | para |
| 126) | 2-Methylpropyl | n-Pentyl | n-Pentyl | 1 | para |
| 127) | 1-Methylpropyl | n-Pentyl | n-Pentyl | 1 | para |
| 128) | 2,2-Dimethylpropyl | n-Pentyl | n-Pentyl | 1 | para |
| 129) | n-Pentyl | n-Pentyl | n-Pentyl | 1 | para |
| 130) | 3-Methylbutyl | n-Pentyl | n-Pentyl | 1 | para |
| 131) | 2-Methylbutyl | n-Pentyl | n-Pentyl | 1 | para |
| 132) | 1-Methylbutyl | n-Pentyl | n-Pentyl | 1 | para |
| 133) | n-Hexyl | n-Pentyl | n-Pentyl | 1 | para |
| 134) | n-Heptyl | n-Pentyl | n-Pentyl | 1 | para |
| 135) | n-Octyl | n-Pentyl | n-Pentyl | 1 | para |
| 136) | 2-Ethylhexyl | n-Pentyl | n-Pentyl | 1 | para |
| 137) | Methyl | n-Hexyl | n-Hexyl | 1 | para |
| 138) | Ethyl | n-Hexyl | n-Hexyl | 1 | para |
| 139) | n-Propyl | n-Hexyl | n-Hexyl | 1 | para |
| 140) | iso-Propyl | n-Hexyl | n-Hexyl | 1 | para |
| 141) | n-Butyl | n-Hexyl | n-Hexyl | 1 | para |
| 142) | 2-Methylpropyl | n-Hexyl | n-Hexyl | 1 | para |
| 143) | 1-Methylpropyl | n-Hexyl | n-Hexyl | 1 | para |
| 144) | 2,2-Dimethylpropyl | n-Hexyl | n-Hexyl | 1 | para |
| 145) | n-Pentyl | n-Hexyl | n-Hexyl | 1 | para |
| 146) | 3-Methylbutyl | n-Hexyl | n-Hexyl | 1 | para |
| 147) | 2-Methylbutyl | n-Hexyl | n-Hexyl | 1 | para |
| 148) | 1-Methylbutyl | n-Hexyl | n-Hexyl | 1 | para |
| 149) | n-Hexyl | n-Hexyl | n-Hexyl | 1 | para |
| 150) | n-Heptyl | n-Hexyl | n-Hexyl | 1 | para |
| 151) | n-Octyl | n-Hexyl | n-Hexyl | 1 | para |
| 152) | 2-Ethylhexyl | n-Hexyl | n-Hexyl | 1 | para |
| 153) | Methyl | Methoxy | Methoxy | 1 | para |
| 154) | Ethyl | Methoxy | Methoxy | 1 | para |
| 155) | n-Propyl | Methoxy | Methoxy | 1 | para |
| 156) | iso-Propyl | Methoxy | Methoxy | 1 | para |
| 157) | n-Butyl | Methoxy | Methoxy | 1 | para |
| 158) | 2-Methylpropyl | Methoxy | Methoxy | 1 | para |
| 159) | 1-Methylpropyl | Methoxy | Methoxy | 1 | para |
| 160) | 2,2-Dimethylpropyl | Methoxy | Methoxy | 1 | para |
| 161) | n-Pentyl | Methoxy | Methoxy | 1 | para |
| 162) | 3-Methylbutyl | Methoxy | Methoxy | 1 | para |
| 163) | 2-Methylbutyl | Methoxy | Methoxy | 1 | para |
| 164) | 1-Methylbutyl | Methoxy | Methoxy | 1 | para |
| 165) | n-Hexyl | Methoxy | Methoxy | 1 | para |
| 166) | n-Heptyl | Methoxy | Methoxy | 1 | para |
| 167) | n-Octyl | Methoxy | Methoxy | 1 | para |
| 168) | 2-Ethylhexyl | Methoxy | Methoxy | 1 | para |
| 169) | Methyl | Ethoxy | Ethoxy | 1 | para |
| 170) | Ethyl | Ethoxy | Ethoxy | 1 | para |
| 171) | n-Propyl | Ethoxy | Ethoxy | 1 | para |
| 172) | iso-Propyl | Ethoxy | Ethoxy | 1 | para |
| 173) | n-Butyl | Ethoxy | Ethoxy | 1 | para |
| 174) | 2-Methylpropyl | Ethoxy | Ethoxy | 1 | para |
| 175) | 1-Methylpropyl | Ethoxy | Ethoxy | 1 | para |
| 176) | 2,2-Dimethylpropyl | Ethoxy | Ethoxy | 1 | para |
| 177) | n-Pentyl | Ethoxy | Ethoxy | 1 | para |
| 178) | 3-Methylbutyl | Ethoxy | Ethoxy | 1 | para |
| 179) | 2-Methylbutyl | Ethoxy | Ethoxy | 1 | para |
| 180) | 1-Methylbutyl | Ethoxy | Ethoxy | 1 | para |
| 181) | n-Hexyl | Ethoxy | Ethoxy | 1 | para |
| 182) | n-Heptyl | Ethoxy | Ethoxy | 1 | para |
| 183) | n-Octyl | Ethoxy | Ethoxy | 1 | para |
| 184) | 2-Ethylhexyl | Ethoxy | Ethoxy | 1 | para |
| 185) | Methyl | Methyl | Methyl | 2 | o/p*) |
| 186) | n-Propyl | Methyl | Methyl | 2 | |
| 187) | iso-Propyl | Methyl | Methyl | 2 | |

TABLE 3-continued

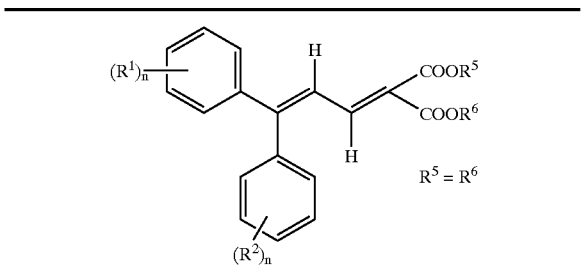

$R^5 = R^6$

| No. | $R^5=R^6$ | $R^1$ | $R^2$ | n | Position |
|---|---|---|---|---|---|
| 188) | n-Butyl | Methyl | Methyl | 2 | |
| 189) | 2-Methylpropyl | Methyl | Methyl | 2 | |
| 190) | 1-Methylpropyl | Methyl | Methyl | 2 | |
| 191) | 2,2-Dimethylpropyl | Methyl | Methyl | 2 | o/p*) |
| 192) | n-Pentyl | Methyl | Methyl | 2 | o/p*) |
| 193) | 3-Methylbutyl | Methyl | Methyl | 2 | o/p*) |
| 194) | 2-Methylbutyl | Methyl | Methyl | 2 | o/p*) |
| 195) | 1-Methylbutyl | Methyl | Methyl | 2 | o/p*) |
| 196) | n-Hexyl | Methyl | Methyl | 2 | o/p*) |
| 197) | n-Heptyl | Methyl | Methyl | 2 | o/p*) |
| 198) | n-Octyl | Methyl | Methyl | 2 | o/p*) |
| 199) | 2-Ethylhexyl | Methyl | Methyl | 2 | o/p*) |
| 200) | Methyl | Ethyl | Ethyl | 2 | o/p*) |
| 201) | Ethyl | Ethyl | Ethyl | 2 | o/p*) |
| 202) | n-Propyl | Ethyl | Ethyl | 2 | o/p*) |
| 203) | iso-Propyl | Ethyl | Ethyl | 2 | o/p*) |
| 204) | n-Butyl | Ethyl | Ethyl | 2 | o/p*) |
| 205) | 2-Methylpropyl | Ethyl | Ethyl | 2 | o/p*) |
| 206) | 1-Methylpropyl | Ethyl | Ethyl | 2 | o/p*) |
| 207) | 2,2-Dimethylpropyl | Ethyl | Ethyl | 2 | o/p*) |
| 208) | n-Pentyl | Ethyl | Ethyl | 2 | o/p*) |
| 209) | 3-Methylbutyl | Ethyl | Ethyl | 2 | o/p*) |
| 210) | 2-Methylbutyl | Ethyl | Ethyl | 2 | o/p*) |
| 211) | 1-Methylbutyl | Ethyl | Ethyl | 2 | o/p*) |
| 212) | n-Hexyl | Ethyl | Ethyl | 2 | o/p*) |
| 213) | n-Heptyl | Ethyl | Ethyl | 2 | o/p*) |
| 214) | n-Octyl | Ethyl | Ethyl | 2 | o/p*) |
| 215) | 2-Ethylhexyl | Ethyl | Ethyl | 2 | o/p*) |
| 216) | Methyl | n-Propyl | n-Propyl | 2 | o/p*) |
| 217) | Ethyl | n-Propyl | n-Propyl | 2 | o/p*) |
| 218) | n-Propyl | n-Propyl | n-Propyl | 2 | o/p*) |
| 219) | iso-Propyl | n-Propyl | n-Propyl | 2 | o/p*) |
| 220) | n-Butyl | n-Propyl | n-Propyl | 2 | o/p*) |
| 221) | 2-Methylpropyl | n-Propyl | n-Propyl | 2 | o/p*) |
| 222) | 1-Methylpropyl | n-Propyl | n-Propyl | 2 | o/p*) |
| 223) | 2,2-Dimethylpropyl | n-Propyl | n-Propyl | 2 | o/p*) |
| 224) | n-Pentyl | n-Propyl | n-Propyl | 2 | o/p*) |
| 225) | 3-Methylbutyl | n-Propyl | n-Propyl | 2 | o/p*) |
| 226) | 2-Methylbutyl | n-Propyl | n-Propyl | 2 | o/p*) |
| 227) | 1-Methylbutyl | n-Propyl | n-Propyl | 2 | o/p*) |
| 228) | n-Hexyl | n-Propyl | n-Propyl | 2 | o/p*) |
| 229) | n-Heptyl | n-Propyl | n-Propyl | 2 | o/p*) |
| 230) | n-Octyl | n-Propyl | n-Propyl | 2 | o/p*) |
| 231) | 2-Ethylhexyl | n-Propyl | n-Propyl | 2 | o/p*) |
| 232) | Methyl | i-Propyl | i-Propyl | 2 | o/p*) |
| 233) | Ethyl | i-Propyl | i-Propyl | 2 | o/p*) |
| 234) | n-Propyl | i-Propyl | i-Propyl | 2 | o/p*) |
| 235) | iso-Propyl | i-Propyl | i-Propyl | 2 | o/p*) |
| 236) | n-Butyl | i-Propyl | i-Propyl | 2 | o/p*) |
| 237) | 2-Methylpropyl | i-Propyl | i-Propyl | 2 | o/p*) |
| 238) | 1-Methylpropyl | i-Propyl | i-Propyl | 2 | o/p*) |
| 239) | 2,2-Dimethylpropyl | i-Propyl | i-Propyl | 2 | o/p*) |
| 240) | n-Pentyl | i-Propyl | i-Propyl | 2 | o/p*) |
| 241) | 3-Methylbutyl | i-Propyl | i-Propyl | 2 | o/p*) |
| 242) | 2-Methylbutyl | i-Propyl | i-Propyl | 2 | o/p*) |
| 243) | 1-Methylbutyl | i-Propyl | i-Propyl | 2 | o/p*) |
| 244) | n-Hexyl | i-Propyl | i-Propyl | 2 | o/p*) |
| 245) | n-Heptyl | i-Propyl | i-Propyl | 2 | o/p*) |
| 246) | n-Octyl | i-Propyl | i-Propyl | 2 | o/p*) |
| 247) | 2-Ethylhexyl | i-Propyl | i-Propyl | 2 | o/p*) |
| 248) | Methyl | n-Butyl | n-Butyl | 2 | o/p*) |
| 249) | Ethyl | n-Butyl | n-Butyl | 2 | o/p*) |
| 250) | n-Propyl | n-Butyl | n-Butyl | 2 | o/p*) |
| 251) | iso-Propyl | n-Butyl | n-Butyl | 2 | o/p*) |
| 252) | n-Butyl | n-Butyl | n-Butyl | 2 | o/p*) |
| 253) | 2-Methylpropyl | n-Butyl | n-Butyl | 2 | o/p*) |
| 254) | 1-Methylpropyl | n-Butyl | n-Butyl | 2 | o/p*) |
| 255) | 2,2-Dimethylpropyl | n-Butyl | n-Butyl | 2 | o/p*) |
| 256) | n-Pentyl | n-Butyl | n-Butyl | 2 | o/p*) |
| 257) | 3-Methylbutyl | n-Butyl | n-Butyl | 2 | o/p*) |
| 258) | 2-Methylbutyl | n-Butyl | n-Butyl | 2 | o/p*) |
| 259) | 1-Methylbutyl | n-Butyl | n-Butyl | 2 | o/p*) |
| 260) | n-Hexyl | n-Butyl | n-Butyl | 2 | o/p*) |
| 261) | n-Heptyl | n-Butyl | n-Butyl | 2 | o/p*) |
| 262) | n-Octyl | n-Butyl | n-Butyl | 2 | o/p*) |
| 263) | 2-Ethylhexyl | n-Butyl | n-Butyl | 2 | o/p*) |
| 264) | Methyl | 1-Methylpropyl | 1-Methylpropyl | 2 | o/p*) |
| 265) | Ethyl | 1-Methylpropyl | 1-Methylpropyl | 2 | o/p*) |
| 266) | n-Propyl | 1-Methylpropyl | 1-Methylpropyl | 2 | o/p*) |
| 267) | iso-Propyl | 1-Methylpropyl | 1-Methylpropyl | 2 | o/p*) |
| 268) | n-Butyl | 1-Methylpropyl | 1-Methylpropyl | 2 | o/p*) |
| 269) | 2-Methylpropyl | 1-Methylpropyl | 1-Methylpropyl | 2 | o/p*) |
| 270) | 1-Methylpropyl | 1-Methylpropyl | 1-Methylpropyl | 2 | o/p*) |
| 271) | 2,2-Dimethylpropyl | 1-Methylpropyl | 1-Methylpropyl | 2 | o/p*) |
| 272) | n-Pentyl | 1-Methylpropyl | 1-Methylpropyl | 2 | o/p*) |
| 273) | 3-Methylbutyl | 1-Methylpropyl | 1-Methylpropyl | 2 | o/p*) |
| 274) | 2-Methylbutyl | 1-Methylpropyl | 1-Methylpropyl | 2 | o/p*) |
| 275) | 1-Methylbutyl | 1-Methylpropyl | 1-Methylpropyl | 2 | o/p*) |
| 276) | n-Hexyl | 1-Methylpropyl | 1-Methylpropyl | 2 | o/p*) |
| 277) | n-Heptyl | 1-Methylpropyl | 1-Methylpropyl | 2 | o/p*) |
| 278) | n-Octyl | 1-Methylpropyl | 1-Methylpropyl | 2 | o/p*) |
| 279) | 2-Ethylhexyl | 1-Methylpropyl | 1-Methylpropyl | 2 | o/p*) |
| 280) | Methyl | 2-Methylpropyl | 2-Methylpropyl | 2 | o/p*) |
| 281) | Ethyl | 2-Methylpropyl | 2-Methylpropyl | 2 | o/p*) |
| 282) | n-Propyl | 2-Methylpropyl | 2-Methylpropyl | 2 | o/p*) |
| 283) | iso-Propyl | 2-Methylpropyl | 2-Methylpropyl | 2 | o/p*) |
| 284) | n-Butyl | 2-Methylpropyl | 2-Methylpropyl | 2 | o/p*) |
| 285) | 2-Methylpropyl | 2-Methylpropyl | 2-Methylpropyl | 2 | o/p*) |
| 286) | 1-Methylpropyl | 2-Methylpropyl | 2-Methylpropyl | 2 | o/p*) |
| 287) | 2,2-Dimethylpropyl | 2-Methylpropyl | 2-Methylpropyl | 2 | o/p*) |
| 288) | n-Pentyl | 2-Methylpropyl | 2-Methylpropyl | 2 | o/p*) |
| 289) | 3-Methylbutyl | 2-Methylpropyl | 2-Methylpropyl | 2 | o/p*) |
| 290) | 2-Methylbutyl | 2-Methylpropyl | 2-Methylpropyl | 2 | o/p*) |
| 291) | 1-Methylbutyl | 2-Methylpropyl | 2-Methylpropyl | 2 | o/p*) |
| 292) | n-Hexyl | 2-Methylpropyl | 2-Methylpropyl | 2 | o/p*) |
| 293) | n-Heptyl | 2-Methylpropyl | 2-Methylpropyl | 2 | o/p*) |
| 294) | n-Octyl | 2-Methylpropyl | 2-Methylpropyl | 2 | o/p*) |
| 295) | 2-Ethylhexyl | 2-Methylpropyl | 2-Methylpropyl | 2 | o/p*) |
| 296) | Methyl | n-Pentyl | n-Pentyl | 2 | |
| 297) | Ethyl | n-Pentyl | n-Pentyl | 2 | |
| 298) | n-Propyl | n-Pentyl | n-Pentyl | 2 | |
| 299) | iso-Propyl | n-Pentyl | n-Pentyl | 2 | o/p*) |
| 300) | n-Butyl | n-Pentyl | n-Pentyl | 2 | o/p*) |
| 301) | 2-Methylpropyl | n-Pentyl | n-Pentyl | 2 | o/p*) |
| 302) | 1-Methylpropyl | n-Pentyl | n-Pentyl | 2 | o/p*) |
| 303) | 2,2-Dimethylpropyl | n-Pentyl | n-Pentyl | 2 | o/p*) |
| 304) | n-Pentyl | n-Pentyl | n-Pentyl | 2 | o/p*) |
| 305) | 3-Methylbutyl | n-Pentyl | n-Pentyl | 2 | o/p*) |
| 306) | 2-Methylbutyl | n-Pentyl | n-Pentyl | 2 | o/p*) |
| 307) | 1-Methylbutyl | n-Pentyl | n-Pentyl | 2 | o/p*) |
| 308) | n-Hexyl | n-Pentyl | n-Pentyl | 2 | o/p*) |
| 309) | n-Heptyl | n-Pentyl | n-Pentyl | 2 | o/p*) |
| 310) | n-Octyl | n-Pentyl | n-Pentyl | 2 | o/p*) |
| 311) | 2-Ethylhexyl | n-Pentyl | n-Pentyl | 2 | o/p*) |

TABLE 3-continued (structure: diphenyl diene with COOR⁵ and COOR⁶ groups; $R^5 = R^6$; phenyl rings bear $(R^1)_n$ and $(R^2)_n$)

| No. | R⁵=R⁶ | R¹ | R² | n | Position |
|---|---|---|---|---|---|
| 312) | Methyl | n-Hexyl | n-Hexyl | 2 | o/p*) |
| 313) | Ethyl | n-Hexyl | n-Hexyl | 2 | o/p*) |
| 314) | n-Propyl | n-Hexyl | n-Hexyl | 2 | o/p*) |
| 315) | iso-Propyl | n-Hexyl | n-Hexyl | 2 | o/p*) |
| 316) | n-Butyl | n-Hexyl | n-Hexyl | 2 | o/p*) |
| 317) | 2-Methylpropyl | n-Hexyl | n-Hexyl | 2 | o/p*) |
| 318) | 1-Methylpropyl | n-Hexyl | n-Hexyl | 2 | o/p*) |
| 319) | 2,2-Dimethylpropyl | n-Hexyl | n-Hexyl | 2 | o/p*) |
| 320) | n-Pentyl | n-Hexyl | n-Hexyl | 2 | o/p*) |
| 321) | 3-Methylbutyl | n-Hexyl | n-Hexyl | 2 | o/p*) |
| 322) | 2-Methylbutyl | n-Hexyl | n-Hexyl | 2 | o/p*) |
| 323) | 1-Methylbutyl | n-Hexyl | n-Hexyl | 2 | o/p*) |
| 324) | n-Hexyl | n-Hexyl | n-Hexyl | 2 | o/p*) |
| 325) | n-Heptyl | n-Hexyl | n-Hexyl | 2 | o/p*) |
| 326) | n-Octyl | n-Hexyl | n-Hexyl | 2 | o/p*) |
| 327) | 2-Ethylhexyl | n-Hexyl | n-Hexyl | 2 | o/p*) |
| 328) | Methyl | Methoxy | Methoxy | 2 | o/p*) |
| 329) | Ethyl | Methoxy | Methoxy | 2 | o/p*) |
| 330) | n-Propyl | Methoxy | Methoxy | 2 | o/p*) |
| 331) | iso-Propyl | Methoxy | Methoxy | 2 | o/p*) |
| 332) | n-Butyl | Methoxy | Methoxy | 2 | o/p*) |
| 333) | 2-Methylpropyl | Methoxy | Methoxy | 2 | o/p*) |
| 334) | 1-Methylpropyl | Methoxy | Methoxy | 2 | o/p*) |
| 335) | 2,2-Dimethylpropyl | Methoxy | Methoxy | 2 | o/p*) |
| 336) | n-Pentyl | Methoxy | Methoxy | 2 | o/p*) |
| 337) | 3-Methylbutyl | Methoxy | Methoxy | 2 | o/p*) |
| 338) | 2-Methylbutyl | Methoxy | Methoxy | 2 | o/p*) |
| 339) | 1-Methylbutyl | Methoxy | Methoxy | 2 | o/p*) |
| 340) | n-Hexyl | Methoxy | Methoxy | 2 | o/p*) |
| 341) | n-Heptyl | Methoxy | Methoxy | 2 | o/p*) |
| 342) | n-Octyl | Methoxy | Methoxy | 2 | o/p*) |
| 343) | 2-Ethylhexyl | Methoxy | Methoxy | 2 | o/p*) |
| 344) | Methyl | Ethoxy | Ethoxy | 2 | o/p*) |
| 345) | Ethyl | Ethoxy | Ethoxy | 2 | o/p*) |
| 346) | n-Propyl | Ethoxy | Ethoxy | 2 | o/p*) |
| 347) | iso-Propyl | Ethoxy | Ethoxy | 2 | o/p*) |
| 348) | n-Butyl | Ethoxy | Ethoxy | 2 | o/p*) |
| 349) | 2-Methylpropyl | Ethoxy | Ethoxy | 2 | o/p*) |
| 350) | 1-Methylpropyl | Ethoxy | Ethoxy | 2 | o/p*) |
| 351) | 2,2-Dimethylpropyl | Ethoxy | Ethoxy | 2 | o/p*) |
| 352) | n-Pentyl | Ethoxy | Ethoxy | 2 | o/p*) |
| 353) | 3-Methylbutyl | Ethoxy | Ethoxy | 2 | o/p*) |
| 354) | 2-Methylbutyl | Ethoxy | Ethoxy | 2 | o/p*) |
| 355) | 1-Methylbutyl | Ethoxy | Ethoxy | 2 | o/p*) |
| 356) | n-Hexyl | Ethoxy | Ethoxy | 2 | o/p*) |
| 357) | n-Heptyl | Ethoxy | Ethoxy | 2 | o/p*) |
| 358) | n-Octyl | Ethoxy | Ethoxy | 2 | o/p*) |
| 359) | 2-Ethylhexyl | Ethoxy | Ethoxy | 2 | o/p*) |

*) o/p represents ortho- and para-substituted

TABLE 4

(structure: diphenyl diene with $CONR^5R^6$ groups; $R^5 = R^6$; phenyl rings bear $(R^1)_n$ and $(R^2)_n$)

| No. | R⁵ = R⁶ | R¹ | R² | n | Position |
|---|---|---|---|---|---|
| 1) | Methyl | H | H | 1 | — |
| 2) | Ethyl | H | H | 1 | — |
| 3) | n-Propyl | H | H | 1 | — |
| 4) | iso-Propyl | H | H | 1 | — |
| 5) | n-Butyl | H | H | 1 | — |
| 6) | 2-Methylpropyl | H | H | 1 | — |
| 7) | 1-Methylpropyl | H | H | 1 | — |
| 8) | 2,2-Dimethylpropyl | H | H | 1 | — |
| 9) | n-Pentyl | H | H | 1 | — |
| 10) | 3-Methylbutyl | H | H | 1 | — |
| 11) | 2-Methylbutyl | H | H | 1 | — |
| 12) | 1-Methylbutyl | H | H | 1 | — |
| 13) | n-Hexyl | H | H | 1 | — |
| 14) | n-Heptyl | H | H | 1 | — |
| 15) | n-Octyl | H | H | 1 | — |
| 16) | 2-Ethylhexyl | H | H | 1 | — |
| 17) | Methyl | Methyl | Methyl | 1 | para |
| 18) | Ethyl | Methyl | Methyl | 1 | para |
| 19) | n-Propyl | Methyl | Methyl | 1 | para |
| 20) | iso-Propyl | Methyl | Methyl | 1 | para |
| 21) | n-Butyl | Methyl | Methyl | 1 | para |
| 22) | 2-Methylpropyl | Methyl | Methyl | 1 | para |
| 23) | 1-Methylpropyl | Methyl | Methyl | 1 | para |
| 24) | 2,2-Dimethylpropyl | Methyl | Methyl | 1 | para |
| 25) | n-Pentyl | Methyl | Methyl | 1 | para |
| 26) | 3-Methylbutyl | Methyl | Methyl | 1 | para |
| 27) | 2-Methylbutyl | Methyl | Methyl | 1 | para |
| 28) | 1-Methylbutyl | Methyl | Methyl | 1 | para |
| 29) | n-Hexyl | Methyl | Methyl | 1 | para |
| 30) | n-Heptyl | Methyl | Methyl | 1 | para |
| 31) | n-Octyl | Methyl | Methyl | 1 | para |
| 32) | 2-Ethylhexyl | Methyl | Methyl | 1 | para |
| 33) | Methyl | Ethyl | Ethyl | 1 | para |
| 34) | Ethyl | Ethyl | Ethyl | 1 | para |
| 35) | n-Propyl | Ethyl | Ethyl | 1 | para |
| 36) | iso-Propyl | Ethyl | Ethyl | 1 | para |
| 37) | n-Butyl | Ethyl | Ethyl | 1 | para |
| 38) | 2-Methylpropyl | Ethyl | Ethyl | 1 | para |
| 39) | 1-Methylpropyl | Ethyl | Ethyl | 1 | para |
| 40) | 2,2-Dimethylpropyl | Ethyl | Ethyl | 1 | para |
| 41) | n-Pentyl | Ethyl | Ethyl | 1 | para |
| 42) | 3-Methylbutyl | Ethyl | Ethyl | 1 | para |
| 43) | 2-Methylbutyl | Ethyl | Ethyl | 1 | para |
| 44) | 1-Methylbutyl | Ethyl | Ethyl | 1 | para |
| 45) | n-Hexyl | Ethyl | Ethyl | 1 | para |
| 46) | n-Heptyl | Ethyl | Ethyl | 1 | para |
| 47) | n-Octyl | Ethyl | Ethyl | 1 | para |
| 48) | 2-Ethylhexyl | Ethyl | Ethyl | 1 | para |
| 49) | Methyl | n-Propyl | n-Propyl | 1 | para |
| 50) | Ethyl | n-Propyl | n-Propyl | 1 | para |
| 51) | n-Propyl | n-Propyl | n-Propyl | 1 | para |
| 52) | iso-Propyl | n-Propyl | n-Propyl | 1 | para |
| 53) | n-Butyl | n-Propyl | n-Propyl | 1 | para |
| 54) | 2-Methylpropyl | n-Propyl | n-Propyl | 1 | para |
| 55) | 1-Methylpropyl | n-Propyl | n-Propyl | 1 | para |
| 56) | 2,2-Dimethylpropyl | n-Propyl | n-Propyl | 1 | para |
| 57) | n-Pentyl | n-Propyl | n-Propyl | 1 | para |
| 58) | 3-Methylbutyl | n-Propyl | n-Propyl | 1 | para |
| 59) | 2-Methylbutyl | n-Propyl | n-Propyl | 1 | para |
| 60) | 1-Methylbutyl | n-Propyl | n-Propyl | 1 | para |
| 61) | n-Hexyl | n-Propyl | n-Propyl | 1 | para |
| 62) | n-Heptyl | n-Propyl | n-Propyl | 1 | para |
| 63) | n-Octyl | n-Propyl | n-Propyl | 1 | para |

TABLE 4-continued

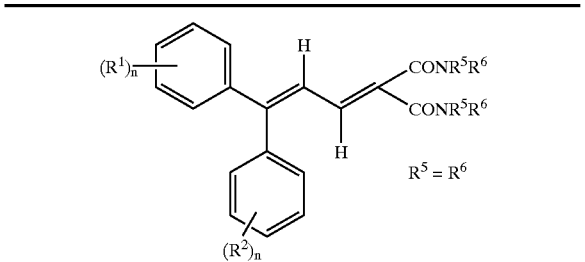

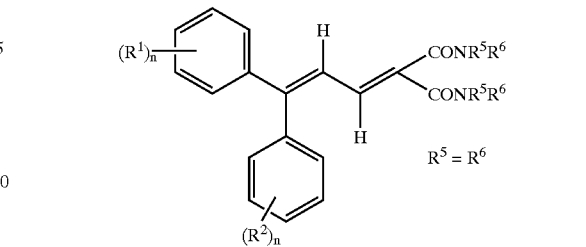

$R^5 = R^6$

| No. | $R^5 = R^6$ | $R^1$ | $R^2$ | n | Position |
|---|---|---|---|---|---|
| 64) | 2-Ethylhexyl | n-Propyl | n-Propyl | 1 | para |
| 65) | Methyl | i-Propyl | i-Propyl | 1 | para |
| 66) | Ethyl | i-Propyl | i-Propyl | 1 | para |
| 67) | n-Propyl | i-Propyl | i-Propyl | 1 | para |
| 68) | iso-Propyl | i-Propyl | i-Propyl | 1 | para |
| 69) | n-Butyl | i-Propyl | i-Propyl | 1 | para |
| 70) | 2-Methylpropyl | i-Propyl | i-Propyl | 1 | para |
| 71) | 1-Methylpropyl | i-Propyl | i-Propyl | 1 | para |
| 72) | 2,2-Dimethylpropyl | i-Propyl | i-Propyl | 1 | para |
| 73) | n-Pentyl | i-Propyl | i-Propyl | 1 | para |
| 74) | 3-Methylbutyl | i-Propyl | i-Propyl | 1 | para |
| 75) | 2-Methylbutyl | i-Propyl | i-Propyl | 1 | para |
| 76) | 1-Methylbutyl | i-Propyl | i-Propyl | 1 | para |
| 77) | n-Hexyl | i-Propyl | i-Propyl | 1 | para |
| 78) | n-Heptyl | i-Propyl | i-Propyl | 1 | para |
| 79) | n-Octyl | i-Propyl | i-Propyl | 1 | para |
| 80) | 2-Ethylhexyl | i-Propyl | i-Propyl | 1 | para |
| 81) | Methyl | n-Butyl | n-Butyl | 1 | para |
| 82) | Ethyl | n-Butyl | n-Butyl | 1 | para |
| 83) | n-Propyl | n-Butyl | n-Butyl | 1 | para |
| 84) | iso-Propyl | n-Butyl | n-Butyl | 1 | para |
| 85) | n-Butyl | n-Butyl | n-Butyl | 1 | para |
| 86) | 2-Methylpropyl | n-Butyl | n-Butyl | 1 | para |
| 87) | 1-Methylpropyl | n-Butyl | n-Butyl | 1 | para |
| 88) | 2,2-Dimethylpropyl | n-Butyl | n-Butyl | 1 | para |
| 89) | n-Pentyl | n-Butyl | n-Butyl | 1 | para |
| 90) | 3-Methylbutyl | n-Butyl | n-Butyl | 1 | para |
| 91) | 2-Methylbutyl | n-Butyl | n-Butyl | 1 | para |
| 92) | 1-Methylbutyl | n-Butyl | n-Butyl | 1 | para |
| 93) | n-Hexyl | n-Butyl | n-Butyl | 1 | para |
| 94) | n-Heptyl | n-Butyl | n-Butyl | 1 | para |
| 95) | n-Octyl | n-Butyl | n-Butyl | 1 | para |
| 96) | 2-Ethylhexyl | n-Butyl | n-Butyl | 1 | para |
| 97) | Methyl | 1-Methylpropyl | 1-Methylpropyl | 1 | para |
| 98) | Ethyl | 1-Methylpropyl | 1-Methylpropyl | 1 | para |
| 99) | n-Propyl | 1-Methylpropyl | 1-Methylpropyl | 1 | para |
| 100) | iso-Propyl | 1-Methylpropyl | 1-Methylpropyl | 1 | para |
| 101) | n-Butyl | 1-Methylpropyl | 1-Methylpropyl | 1 | para |
| 102) | 2-Methylpropyl | 1-Methylpropyl | 1-Methylpropyl | 1 | para |
| 103) | 1-Methylpropyl | 1-Methylpropyl | 1-Methylpropyl | 1 | para |
| 104) | 2,2-Dimethylpropyl | 1-Methylpropyl | 1-Methylpropyl | 1 | para |
| 105) | n-Pentyl | 1-Methylpropyl | 1-Methylpropyl | 1 | para |
| 106) | 3-Methylbutyl | 1-Methylpropyl | 1-Methylpropyl | 1 | para |
| 107) | 2-Methylbutyl | 1-Methylpropyl | 1-Methylpropyl | 1 | para |
| 108) | 1-Methylbutyl | 1-Methylpropyl | 1-Methylpropyl | 1 | para |
| 109) | n-Hexyl | 1-Methylpropyl | 1-Methylpropyl | 1 | para |
| 110) | n-Heptyl | 1-Methylpropyl | 1-Methylpropyl | 1 | para |
| 111) | n-Octyl | 1-Methylpropyl | 1-Methylpropyl | 1 | para |
| 112) | 2-Ethylhexyl | 1-Methylpropyl | 1-Methylpropyl | 1 | para |
| 113) | Methyl | 2-Methylpropyl | 2-Methylpropyl | 1 | para |
| 114) | Ethyl | 2-Methylpropyl | 2-Methylpropyl | 1 | para |
| 115) | n-Propyl | 2-Methylpropyl | 2-Methylpropyl | 1 | para |
| 116) | iso-Propyl | 2-Methylpropyl | 2-Methylpropyl | 1 | para |
| 117) | n-Butyl | 2-Methylpropyl | 2-Methylpropyl | 1 | para |
| 118) | 2-Methylpropyl | 2-Methylpropyl | 2-Methylpropyl | 1 | para |
| 119) | 1-Methylpropyl | 2-Methylpropyl | 2-Methylpropyl | 1 | para |
| 120) | 2,2-Dimethylpropyl | 2-Methylpropyl | 2-Methylpropyl | 1 | para |
| 121) | n-Pentyl | 2-Methylpropyl | 2-Methylpropyl | 1 | para |
| 122) | 3-Methylbutyl | 2-Methylpropyl | 2-Methylpropyl | 1 | para |
| 123) | 2-Methylbutyl | 2-Methylpropyl | 2-Methylpropyl | 1 | para |
| 124) | 1-Methylbutyl | 2-Methylpropyl | 2-Methylpropyl | 1 | para |
| 125) | n-Hexyl | 2-Methylpropyl | 2-Methylpropyl | 1 | para |
| 126) | n-Heptyl | 2-Methylpropyl | 2-Methylpropyl | 1 | para |
| 127) | n-Octyl | 2-Methylpropyl | 2-Methylpropyl | 1 | para |
| 128) | 2-Ethylhexyl | 2-Methylpropyl | 2-Methylpropyl | 1 | para |
| 129) | Methyl | n-Pentyl | n-Pentyl | 1 | para |
| 130) | Ethyl | n-Pentyl | n-Pentyl | 1 | para |
| 131) | n-Propyl | n-Pentyl | n-Pentyl | 1 | para |
| 132) | iso-Propyl | n-Pentyl | n-Pentyl | 1 | para |
| 133) | n-Butyl | n-Pentyl | n-Pentyl | 1 | para |
| 134) | 2-Methylpropyl | n-Pentyl | n-Pentyl | 1 | para |
| 135) | 1-Methylpropyl | n-Pentyl | n-Pentyl | 1 | para |
| 136) | 2,2-Dimethylpropyl | n-Pentyl | n-Pentyl | 1 | para |
| 137) | n-Pentyl | n-Pentyl | n-Pentyl | 1 | para |
| 138) | 3-Methylbutyl | n-Pentyl | n-Pentyl | 1 | para |
| 139) | 2-Methylbutyl | n-Pentyl | n-Pentyl | 1 | para |
| 140) | 1-Methylbutyl | n-Pentyl | n-Pentyl | 1 | para |
| 141) | n-Hexyl | n-Pentyl | n-Pentyl | 1 | para |
| 142) | n-Heptyl | n-Pentyl | n-Pentyl | 1 | para |
| 143) | n-Octyl | n-Pentyl | n-Pentyl | 1 | para |
| 144) | 2-Ethylhexyl | n-Pentyl | n-Pentyl | 1 | para |
| 145) | Methyl | n-Hexyl | n-Hexyl | 1 | para |
| 146) | Ethyl | n-Hexyl | n-Hexyl | 1 | para |
| 147) | n-Propyl | n-Hexyl | n-Hexyl | 1 | para |
| 148) | iso-Propyl | n-Hexyl | n-Hexyl | 1 | para |
| 149) | n-Butyl | n-Hexyl | n-Hexyl | 1 | para |
| 150) | 2-Methylpropyl | n-Hexyl | n-Hexyl | 1 | para |
| 151) | 1-Methylpropyl | n-Hexyl | n-Hexyl | 1 | para |
| 152) | 2,2-Dimethylpropyl | n-Hexyl | n-Hexyl | 1 | para |
| 153) | n-Pentyl | n-Hexyl | n-Hexyl | 1 | para |
| 154) | 3-Methylbutyl | n-Hexyl | n-Hexyl | 1 | para |
| 155) | 2-Methylbutyl | n-Hexyl | n-Hexyl | 1 | para |
| 156) | 1-Methylbutyl | n-Hexyl | n-Hexyl | 1 | para |
| 157) | n-Hexyl | n-Hexyl | n-Hexyl | 1 | para |
| 158) | n-Heptyl | n-Hexyl | n-Hexyl | 1 | para |
| 159) | n-Octyl | n-Hexyl | n-Hexyl | 1 | para |
| 160) | 2-Ethylhexyl | n-Hexyl | n-Hexyl | 1 | para |
| 161) | Methyl | Methoxy | Methoxy | 1 | para |
| 162) | Ethyl | Methoxy | Methoxy | 1 | para |
| 163) | n-Propyl | Methoxy | Methoxy | 1 | para |
| 164) | iso-Propyl | Methoxy | Methoxy | 1 | para |
| 165) | n-Butyl | Methoxy | Methoxy | 1 | para |
| 166) | 2-Methylpropyl | Methoxy | Methoxy | 1 | para |
| 167) | 1-Methylpropyl | Methoxy | Methoxy | 1 | para |
| 168) | 2,2-Dimethylpropyl | Methoxy | Methoxy | 1 | para |
| 169) | n-Pentyl | Methoxy | Methoxy | 1 | para |
| 170) | 3-Methylbutyl | Methoxy | Methoxy | 1 | para |
| 171) | 2-Methylbutyl | Methoxy | Methoxy | 1 | para |
| 172) | 1-Methylbutyl | Methoxy | Methoxy | 1 | para |
| 173) | n-Hexyl | Methoxy | Methoxy | 1 | para |
| 174) | n-Heptyl | Methoxy | Methoxy | 1 | para |
| 175) | n-Octyl | Methoxy | Methoxy | 1 | para |
| 176) | 2-Ethylhexyl | Methoxy | Methoxy | 1 | para |
| 177) | Methyl | Ethoxy | Ethoxy | 1 | para |
| 178) | Ethyl | Ethoxy | Ethoxy | 1 | para |
| 179) | n-Propyl | Ethoxy | Ethoxy | 1 | para |
| 180) | iso-Propyl | Ethoxy | Ethoxy | 1 | para |
| 181) | n-Butyl | Ethoxy | Ethoxy | 1 | para |
| 182) | 2-Methylpropyl | Ethoxy | Ethoxy | 1 | para |
| 183) | 1-Methylpropyl | Ethoxy | Ethoxy | 1 | para |
| 184) | 2,2-Dimethylpropyl | Ethoxy | Ethoxy | 1 | para |
| 185) | n-Pentyl | Ethoxy | Ethoxy | 1 | para |
| 186) | 3-Methylbutyl | Ethoxy | Ethoxy | 1 | para |
| 187) | 2-Methylbutyl | Ethoxy | Ethoxy | 1 | para |
| 188) | 1-Methylbutyl | Ethoxy | Ethoxy | 1 | para |
| 189) | n-Hexyl | Ethoxy | Ethoxy | 1 | para |

TABLE 4-continued

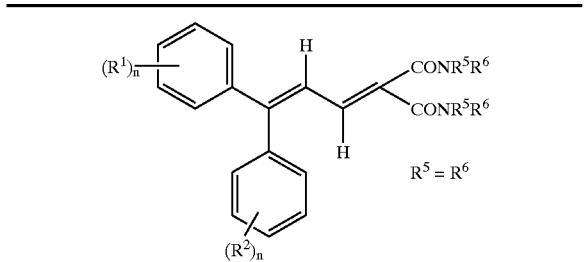

$R^5 = R^6$

| No. | $R^5 = R^6$ | $R^1$ | $R^2$ | n | Position |
|---|---|---|---|---|---|
| 190) | n-Heptyl | Ethoxy | Ethoxy | 1 | para |
| 191) | n-Octyl | Ethoxy | Ethoxy | 1 | para |
| 192) | 2-Ethylhexyl | Ethoxy | Ethoxy | 1 | para |
| 193) | Methyl | Methyl | Methyl | 2 | o/p*) |
| 194) | Ethyl | Methyl | Methyl | 2 | o/p*) |
| 195) | n-Propyl | Methyl | Methyl | 2 | o/p*) |
| 196) | iso-Propyl | Methyl | Methyl | 2 | o/p*) |
| 197) | n-Butyl | Methyl | Methyl | 2 | o/p*) |
| 198) | 2-Methylpropyl | Methyl | Methyl | 2 | o/p*) |
| 199) | 1-Methylpropyl | Methyl | Methyl | 2 | o/p*) |
| 200) | 2,2-Dimethylpropyl | Methyl | Methyl | 2 | o/p*) |
| 201) | n-Pentyl | Methyl | Methyl | 2 | o/p*) |
| 202) | 3-Methylbutyl | Methyl | Methyl | 2 | o/p*) |
| 203) | 2-Methylbutyl | Methyl | Methyl | 2 | o/p*) |
| 204) | 1-Methylbutyl | Methyl | Methyl | 2 | o/p*) |
| 205) | n-Hexyl | Methyl | Methyl | 2 | o/p*) |
| 206) | n-Heptyl | Methyl | Methyl | 2 | o/p*) |
| 207) | n-Octyl | Methyl | Methyl | 2 | o/p*) |
| 208) | 2-Ethylhexyl | Methyl | Methyl | 2 | o/p*) |
| 209) | Methyl | Ethyl | Ethyl | 2 | o/p*) |
| 210) | Ethyl | Ethyl | Ethyl | 2 | o/p*) |
| 211) | n-Propyl | Ethyl | Ethyl | 2 | o/p*) |
| 212) | iso-Propyl | Ethyl | Ethyl | 2 | o/p*) |
| 213) | n-Butyl | Ethyl | Ethyl | 2 | o/p*) |
| 214) | 2-Methylpropyl | Ethyl | Ethyl | 2 | o/p*) |
| 215) | 1-Methylpropyl | Ethyl | Ethyl | 2 | o/p*) |
| 216) | 2,2-Dimethylpropyl | Ethyl | Ethyl | 2 | o/p*) |
| 217) | n-Pentyl | Ethyl | Ethyl | 2 | o/p*) |
| 218) | 3-Methylbutyl | Ethyl | Ethyl | 2 | o/p*) |
| 219) | 2-Methylbutyl | Ethyl | Ethyl | 2 | o/p*) |
| 220) | 1-Methylbutyl | Ethyl | Ethyl | 2 | o/p*) |
| 221) | n-Hexyl | Ethyl | Ethyl | 2 | o/p*) |
| 222) | n-Heptyl | Ethyl | Ethyl | 2 | o/p*) |
| 223) | n-Octyl | Ethyl | Ethyl | 2 | o/p*) |
| 224) | 2-Ethylhexyl | Ethyl | Ethyl | 2 | o/p*) |
| 225) | Methyl | n-Propyl | n-Propyl | 2 | o/p*) |
| 226) | Ethyl | n-Propyl | n-Propyl | 2 | o/p*) |
| 227) | n-Propyl | n-Propyl | n-Propyl | 2 | o/p*) |
| 228) | iso-Propyl | n-Propyl | n-Propyl | 2 | o/p*) |
| 229) | n-Butyl | n-Propyl | n-Propyl | 2 | o/p*) |
| 230) | 2-Methylpropyl | n-Propyl | n-Propyl | 2 | o/p*) |
| 231) | 1-Methylpropyl | n-Propyl | n-Propyl | 2 | o/p*) |
| 232) | 2,2-Dimethylpropyl | n-Propyl | n-Propyl | 2 | o/p*) |
| 233) | n-Pentyl | n-Propyl | n-Propyl | 2 | o/p*) |
| 234) | 3-Methylbutyl | n-Propyl | n-Propyl | 2 | o/p*) |
| 235) | 2-Methylbutyl | n-Propyl | n-Propyl | 2 | o/p*) |
| 236) | 1-Methylbutyl | n-Propyl | n-Propyl | 2 | o/p*) |
| 237) | n-Hexyl | n-Propyl | n-Propyl | 2 | o/p*) |
| 238) | n-Heptyl | n-Propyl | n-Propyl | 2 | o/p*) |
| 239) | n-Octyl | n-Propyl | n-Propyl | 2 | o/p*) |
| 240) | 2-Ethylhexyl | n-Propyl | n-Propyl | 2 | o/p*) |
| 241) | Methyl | i-Propyl | i-Propyl | 2 | o/p*) |
| 242) | Ethyl | i-Propyl | i-Propyl | 2 | o/p*) |
| 243) | n-Propyl | i-Propyl | i-Propyl | 2 | o/p*) |
| 244) | iso-Propyl | i-Propyl | i-Propyl | 2 | o/p*) |
| 245) | n-Butyl | i-Propyl | i-Propyl | 2 | o/p*) |
| 246) | 2-Methylpropyl | i-Propyl | i-Propyl | 2 | o/p*) |
| 247) | 1-Methylpropyl | i-Propyl | i-Propyl | 2 | o/p*) |
| 248) | 2,2-Dimethylpropyl | i-Propyl | i-Propyl | 2 | o/p*) |
| 249) | n-Pentyl | i-Propyl | i-Propyl | 2 | o/p*) |
| 250) | 3-Methylbutyl | i-Propyl | i-Propyl | 2 | o/p*) |
| 251) | 2-Methylbutyl | i-Propyl | i-Propyl | 2 | o/p*) |
| 252) | 1-Methylbutyl | i-Propyl | i-Propyl | 2 | o/p*) |
| 253) | n-Hexyl | i-Propyl | i-Propyl | 2 | o/p*) |
| 254) | n-Heptyl | i-Propyl | i-Propyl | 2 | o/p*) |
| 255) | n-Octyl | i-Propyl | i-Propyl | 2 | o/p*) |
| 256) | 2-Ethylhexyl | i-Propyl | i-Propyl | 2 | o/p*) |
| 257) | Methyl | n-Butyl | n-Butyl | 2 | o/p*) |
| 258) | Ethyl | n-Butyl | n-Butyl | 2 | o/p*) |
| 259) | n-Propyl | n-Butyl | n-Butyl | 2 | o/p*) |
| 260) | iso-Propyl | n-Butyl | n-Butyl | 2 | o/p*) |
| 261) | n-Butyl | n-Butyl | n-Butyl | 2 | o/p*) |
| 262) | 2-Methylpropyl | n-Butyl | n-Butyl | 2 | o/p*) |
| 263) | 1-Methylpropyl | n-Butyl | n-Butyl | 2 | o/p*) |
| 264) | 2,2-Dimethylpropyl | n-Butyl | n-Butyl | 2 | o/p*) |
| 265) | n-Pentyl | n-Butyl | n-Butyl | 2 | o/p*) |
| 266) | 3-Methylbutyl | n-Butyl | n-Butyl | 2 | o/p*) |
| 267) | 2-Methylbutyl | n-Butyl | n-Butyl | 2 | o/p*) |
| 268) | 1-Methylbutyl | n-Butyl | n-Butyl | 2 | o/p*) |
| 269) | n-Hexyl | n-Butyl | n-Butyl | 2 | o/p*) |
| 270) | n-Heptyl | n-Butyl | n-Butyl | 2 | o/p*) |
| 271) | n-Octyl | n-Butyl | n-Butyl | 2 | o/p*) |
| 272) | 2-Ethylhexyl | n-Butyl | n-Butyl | 2 | o/p*) |
| 273) | Methyl | 1-Methylpropyl | 1-Methylpropyl | 2 | o/p*) |
| 274) | Ethyl | 1-Methylpropyl | 1-Methylpropyl | 2 | o/p*) |
| 275) | n-Propyl | 1-Methylpropyl | 1-Methylpropyl | 2 | o/p*) |
| 276) | iso-Propyl | 1-Methylpropyl | 1-Methylpropyl | 2 | o/p*) |
| 277) | n-Butyl | 1-Methylpropyl | 1-Methylpropyl | 2 | o/p*) |
| 278) | 2-Methylpropyl | 1-Methylpropyl | 1-Methylpropyl | 2 | o/p*) |
| 279) | 1-Methylpropyl | 1-Methylpropyl | 1-Methylpropyl | 2 | o/p*) |
| 280) | 2,2-Dimethylpropyl | 1-Methylpropyl | 1-Methylpropyl | 2 | o/p*) |
| 281) | n-Pentyl | 1-Methylpropyl | 1-Methylpropyl | 2 | o/p*) |
| 282) | 3-Methylbutyl | 1-Methylpropyl | 1-Methylpropyl | 2 | o/p*) |
| 283) | 2-Methylbutyl | 1-Methylpropyl | 1-Methylpropyl | 2 | o/p*) |
| 284) | 1-Methylbutyl | 1-Methylpropyl | 1-Methylpropyl | 2 | o/p*) |
| 285) | n-Hexyl | 1-Methylpropyl | 1-Methylpropyl | 2 | o/p*) |
| 286) | n-Heptyl | 1-Methylpropyl | 1-Methylpropyl | 2 | o/p*) |
| 287) | n-Octyl | 1-Methylpropyl | 1-Methylpropyl | 2 | o/p*) |
| 288) | 2-Ethylhexyl | 1-Methylpropyl | 1-Methylpropyl | 2 | o/p*) |
| 289) | Methyl | 2-Methylpropyl | 2-Methylpropyl | 2 | o/p*) |
| 290) | Ethyl | 2-Methylpropyl | 2-Methylpropyl | 2 | o/p*) |
| 291) | n-Propyl | 2-Methylpropyl | 2-Methylpropyl | 2 | o/p*) |
| 292) | iso-Propyl | 2-Methylpropyl | 2-Methylpropyl | 2 | o/p*) |
| 293) | n-Butyl | 2-Methylpropyl | 2-Methylpropyl | 2 | o/p*) |
| 294) | 2-Methylpropyl | 2-Methylpropyl | 2-Methylpropyl | 2 | o/p*) |
| 295) | 1-Methylpropyl | 2-Methylpropyl | 2-Methylpropyl | 2 | o/p*) |
| 296) | 2,2-Dimethylpropyl | 2-Methylpropyl | 2-Methylpropyl | 2 | o/p*) |
| 297) | n-Pentyl | 2-Methylpropyl | 2-Methylpropyl | 2 | o/p*) |
| 298) | 3-Methylbutyl | 2-Methylpropyl | 2-Methylpropyl | 2 | o/p*) |
| 299) | 2-Methylbutyl | 2-Methylpropyl | 2-Methylpropyl | 2 | o/p*) |
| 300) | 1-Methylbutyl | 2-Methylpropyl | 2-Methylpropyl | 2 | o/p*) |
| 301) | n-Hexyl | 2-Methylpropyl | 2-Methylpropyl | 2 | o/p*) |
| 302) | n-Heptyl | 2-Methylpropyl | 2-Methylpropyl | 2 | o/p*) |
| 303) | n-Octyl | 2-Methylpropyl | 2-Methylpropyl | 2 | o/p*) |
| 304) | 2-Ethylhexyl | 2-Methylpropyl | 2-Methylpropyl | 2 | o/p*) |
| 305) | Methyl | n-Pentyl | n-Pentyl | 2 | o/p*) |
| 306) | Ethyl | n-Pentyl | n-Pentyl | 2 | o/p*) |
| 307) | n-Propyl | n-Pentyl | n-Pentyl | 2 | o/p*) |
| 308) | iso-Propyl | n-Pentyl | n-Pentyl | 2 | o/p*) |
| 309) | n-Butyl | n-Pentyl | n-Pentyl | 2 | o/p*) |
| 310) | 2-Methylpropyl | n-Pentyl | n-Pentyl | 2 | o/p*) |
| 311) | 1-Methylpropyl | n-Pentyl | n-Pentyl | 2 | o/p*) |
| 312) | 2,2-Dimethylpropyl | n-Pentyl | n-Pentyl | 2 | o/p*) |
| 313) | n-Pentyl | n-Pentyl | n-Pentyl | 2 | o/p*) |
| 314) | 3-Methylbutyl | n-Pentyl | n-Pentyl | 2 | o/p*) |
| 315) | 2-Methylbutyl | n-Pentyl | n-Pentyl | 2 | o/p*) |

TABLE 4-continued

![Structure with (R¹)ₙ phenyl, H, CONR⁵R⁶ groups, R⁵ = R⁶]

| No. | R⁵ = R⁶ | R¹ | R² | n | Position |
|---|---|---|---|---|---|
| 316) | 1-Methylbutyl | n-Pentyl | n-Pentyl | 2 | o/p*) |
| 317) | n-Hexyl | n-Pentyl | n-Pentyl | 2 | o/p*) |
| 318) | n-Heptyl | n-Pentyl | n-Pentyl | 2 | o/p*) |
| 319) | n-Octyl | n-Pentyl | n-Pentyl | 2 | o/p*) |
| 320) | 2-Ethylhexyl | n-Pentyl | n-Pentyl | 2 | o/p*) |
| 321) | Methyl | n-Hexyl | n-Hexyl | 2 | o/p*) |
| 322) | Ethyl | n-Hexyl | n-Hexyl | 2 | o/p*) |
| 323) | n-Propyl | n-Hexyl | n-Hexyl | 2 | o/p*) |
| 324) | iso-Propyl | n-Hexyl | n-Hexyl | 2 | o/p*) |
| 325) | n-Butyl | n-Hexyl | n-Hexyl | 2 | o/p*) |
| 326) | 2-Methylpropyl | n-Hexyl | n-Hexyl | 2 | o/p*) |
| 327) | 1-Methylpropyl | n-Hexyl | n-Hexyl | 2 | o/p*) |
| 328) | 2,2-Dimethylpropyl | n-Hexyl | n-Hexyl | 2 | o/p*) |
| 329) | n-Pentyl | n-Hexyl | n-Hexyl | 2 | o/p*) |
| 330) | 3-Methylbutyl | n-Hexyl | n-Hexyl | 2 | o/p*) |
| 331) | 2-Methylbutyl | n-Hexyl | n-Hexyl | 2 | o/p*) |
| 332) | 1-Methylbutyl | n-Hexyl | n-Hexyl | 2 | o/p*) |
| 333) | n-Hexyl | n-Hexyl | n-Hexyl | 2 | o/p*) |
| 334) | n-Heptyl | n-Hexyl | n-Hexyl | 2 | o/p*) |
| 335) | n-Octyl | n-Hexyl | n-Hexyl | 2 | o/p*) |
| 336) | 2-Ethylhexyl | n-Hexyl | n-Hexyl | 2 | o/p*) |
| 337) | Methyl | Methoxy | Methoxy | 2 | o/p*) |
| 338) | Ethyl | Methoxy | Methoxy | 2 | o/p*) |
| 339) | n-Propyl | Methoxy | Methoxy | 2 | o/p*) |
| 340) | iso-Propyl | Methoxy | Methoxy | 2 | o/p*) |
| 341) | n-Butyl | Methoxy | Methoxy | 2 | o/p*) |
| 342) | 2-Methylpropyl | Methoxy | Methoxy | 2 | o/p*) |
| 343) | 1-Methylpropyl | Methoxy | Methoxy | 2 | o/p*) |
| 344) | 2,2-Dimethylpropyl | Methoxy | Methoxy | 2 | o/p*) |
| 345) | n-Pentyl | Methoxy | Methoxy | 2 | o/p*) |
| 346) | 3-Methylbutyl | Methoxy | Methoxy | 2 | o/p*) |
| 347) | 2-Methylbutyl | Methoxy | Methoxy | 2 | o/p*) |
| 348) | 1-Methylbutyl | Methoxy | Methoxy | 2 | o/p*) |
| 349) | n-Hexyl | Methoxy | Methoxy | 2 | o/p*) |
| 350) | n-Heptyl | Methoxy | Methoxy | 2 | o/p*) |
| 351) | n-Octyl | Methoxy | Methoxy | 2 | o/p*) |
| 352) | 2-Ethylhexyl | Methoxy | Methoxy | 2 | o/p*) |
| 353) | Methyl | Ethoxy | Ethoxy | 2 | o/p*) |
| 354) | Ethyl | Ethoxy | Ethoxy | 2 | o/p*) |
| 355) | n-Propyl | Ethoxy | Ethoxy | 2 | o/p*) |
| 356) | iso-Propyl | Ethoxy | Ethoxy | 2 | o/p*) |
| 357) | n-Butyl | Ethoxy | Ethoxy | 2 | o/p*) |
| 358) | 2-Methylpropyl | Ethoxy | Ethoxy | 2 | o/p*) |
| 359) | 1-Methylpropyl | Ethoxy | Ethoxy | 2 | o/p*) |
| 360) | 2,2-Dimethylpropyl | Ethoxy | Ethoxy | 2 | o/p*) |
| 361) | n-Pentyl | Ethoxy | Ethoxy | 2 | o/p*) |
| 362) | 3-Methylbutyl | Ethoxy | Ethoxy | 2 | o/p*) |
| 363) | 2-Methylbutyl | Ethoxy | Ethoxy | 2 | o/p*) |
| 364) | 1-Methylbutyl | Ethoxy | Ethoxy | 2 | o/p*) |
| 365) | n-Hexyl | Ethoxy | Ethoxy | 2 | o/p*) |
| 366) | n-Heptyl | Ethoxy | Ethoxy | 2 | o/p*) |
| 367) | n-Octyl | Ethoxy | Ethoxy | 2 | o/p*) |
| 368) | 2-Ethylhexyl | Ethoxy | Ethoxy | 2 | o/p*) |

*) o/p represents ortho- and para-substituted

Example 4
Standardized Methods for Photostability Determination (Suntest)

A 5% by weight alcoholic solution of the sunscreen to be tested is applied, using an Eppendorf pipette (20 µl), to the milled area on a glass plate. Owing to the presence of the alcohol, the solution is distributed uniformly on the roughened glass surface. The amount applied corresponds to the amount of sunscreen required to obtain an average sun protection factor in suncreams. In the test, 4 glass plates are irradiated each time. The evaporation time and the irradiation each last for 30 minutes. The glass plates are cooled slightly during the irradiation by a water cooling system located at the base of the Suntest apparatus. The temperature inside the Suntest apparatus during the irradiation is 40° C. After the samples have been irradiated, they are washed with ethanol into a dark 50 ml graduated flask and measured in a photometer. The blank samples are applied in the same way to glass plates and evaporated at room temperature for 30 minutes. Like the other samples, they are washed off with ethanol and diluted to 100 ml and measured.

Photostability Comparative Tests:

Photostability comparitive tests:

1.

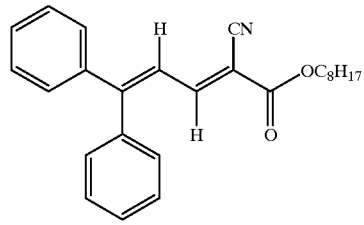

Photostability: 98%

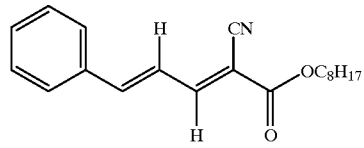

Photostability: 0%

2.

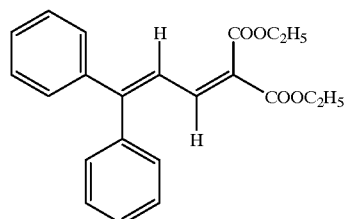

Photostability: 98%

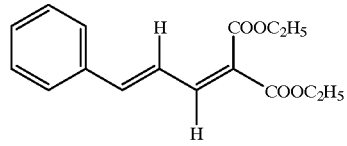

Photostability: 27%

General Method for Preparing Emulsions for Cosmetic Purposes

All the oil-soluble ingredients are heated to 85° C. in a stirred vessel. When all the ingredients have melted or are present as liquid phase, the aqueous phase is incorporated by homogenization. The emulsion is cooled to about 40° C. with stirring, is perfumed and homogenized, and is then cooled to 25° C. while stirring continuously.

Preparations

| Mass content (% by weight) | |
|---|---|
| Example 5 Lip care composition | |
| ad 100 | eucerinum anhydricum |
| 10.00 | glycerol |
| 10.00 | titanium dioxide |
| 5.00 | compound No. 1 in Table 2 |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |
| Example 6 Lip care composition | |
| ad 100 | eucerinum anhydricum |
| 10.00 | glycerol |
| 10.00 | titanium dioxide |
| 5.00 | compound No. 20 in Table 2 |
| 8.00 | octyl methoxycinnamate |
| 5.00 | zinc oxide |
| 4.00 | castor oil |
| 4.00 | pentaerythrityl stearate/caprate/caprylate/adipate |
| 3.00 | glyceryl stearate SE |
| 2.00 | beeswax |
| 2.00 | microcrystalline wax |
| 2.00 | quaternium-18 bentonite |
| 1.50 | PEG-45/dodecyl glycol copolymer |
| Example 7 Sunblocker composition with micropigments | |
| ad 100 | water |
| 10.00 | octyl methoxycinnamate |
| 6.00 | PEG-7 hydrogenated castor oil |
| 6.00 | titanium dioxide |
| 5.00 | compound No. 1 in Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |
| Example 8 Sunblocker composition with micropigments | |
| ad 100 | water |
| 10.00 | octyl methoxycinnamate |
| 6.00 | PEG-7 hydrogenated castor oil |
| 6.00 | titanium dioxide |
| 5.00 | compound No. 20 in Table 2 |
| 5.00 | mineral oil |
| 5.00 | isoamyl p-methoxycinnamate |
| 5.00 | propylene glycol |
| 3.00 | jojoba oil |
| 3.00 | 4-methylbenzylidenecamphor |
| 2.00 | PEG-45/dodecyl glycol copolymer |
| 1.00 | dimethicone |
| 0.50 | PEG-40 hydrogenated castor oil |
| 0.50 | tocopheryl acetate |
| 0.50 | phenoxyethanol |
| 0.20 | EDTA |

-continued

| Mass content (% by weight) | |
|---|---|
| Example 9 Non-greasy gel | |
| ad 100 | water |
| 8.00 | octyl methoxycinnamate |
| 7.00 | titanium dioxide |
| 5.00 | compound No. 1 in Table 2 |
| 5.00 | glycerol |
| 5.00 | PEG-25 PABA |
| 1.00 | 4-methylbenzylidenecamphor |
| 0.40 | acrylate C10–C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |
| Example 10 Non-greasy gel | |
| ad 100 | water |
| 8.00 | octyl methoxycinnamate |
| 7.00 | titanium dioxide |
| 5.00 | compound No. 20 in Table 2 |
| 5.00 | glycerol |
| 5.00 | PEG-25 PABA |
| 1.00 | 4-methylbenzylidenecamphor |
| 0.40 | acrylate C10–C30 alkyl acrylate crosspolymer |
| 0.30 | imidazolidinylurea |
| 0.25 | hydroxyethylcellulose |
| 0.25 | sodium methylparaben |
| 0.20 | disodium EDTA |
| 0.15 | fragrance |
| 0.15 | sodium propylparaben |
| 0.10 | sodium hydroxide |
| Example 11 Suncream (SPF 20) | |
| ad 100 | water |
| 8.00 | octylmethoxycinnamate |
| 8.00 | titanium dioxide |
| 6.00 | PEG-7 hydrogenated castor oil |
| 5.00 | compound No. 1 in Table 2 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |
| Example 12 Suncream (SPF 20) | |
| ad 100 | water |
| 8.00 | octylmethoxycinnamate |
| 8.00 | titanium dioxide |
| 6.00 | PEG-7 hydrogenated castor oil |
| 5.00 | compound No. 20 in Table 2 |
| 6.00 | mineral oil |
| 5.00 | zinc oxide |
| 5.00 | isopropyl palmitate |
| 5.00 | imidazolidinylurea |
| 3.00 | jojoba oil |
| 2.00 | PEG-45/dodecyl glycol copolymer |
| 1.00 | 4-methylbenzylidenecamphor |
| 0.60 | magnesium stearate |
| 0.50 | tocopheryl acetate |
| 0.25 | methylparaben |
| 0.20 | disodium EDTA |
| 0.15 | propylparaben |

-continued

| Mass content (% by weight) | |
|---|---|
| Example 13 Water-resistant suncream | |
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound No. 1 in Table 2 |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |
| Example 14 Water-resistant suncream | |
| ad 100 | water |
| 8.00 | octyl methoxycinnamate |
| 5.00 | PEG-7 hydrogenated castor oil |
| 5.00 | propylene glycol |
| 4.00 | isopropyl palmitate |
| 4.00 | caprylic/capric triglyceride |
| 5.00 | compound No. 20 in Table 2 |
| 4.00 | glycerol |
| 3.00 | jojoba oil |
| 2.00 | 4-methylbenzylidenecamphor |
| 2.00 | titanium dioxide |
| 1.50 | PEG-45/dodecyl glycol copolymer |
| 1.50 | dimethicone |
| 0.70 | magnesium sulfate |
| 0.50 | magnesium stearate |
| 0.15 | fragrance |
| Example 15 Sunmilk (SPF 6) | |
| ad 100 | water |
| 10.00 | mineral oil |
| 6.00 | PEG-7 hydrogenated castor oil |
| 5.00 | isopropyl palmitate |
| 3.50 | octyl methoxycinnamate |
| 5.00 | compound No. 1 in Table 2 |
| 3.00 | caprylic/capric triglyceride |
| 3.00 | jojoba oil |
| 2.00 | PEG-45/dodecyl glycol copolymer |

We claim:

1. A 4,4-diarylbutadiene of the formula Ia,

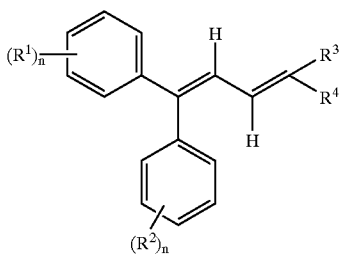

Ia where the diene system has the Z,Z; Z,E; E,Z or E,E configuration or a mixture thereof, and where the variables independently of one another have the following meanings:

$R^1$ and $R^2$ are hydrogen, or are selected from the group consisting of $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl, hetaryl, any of which may be unsubstituted or substituted, and substituents which confer solubility in water and are selected from the group consisting of carboxylate, sulfonate, and ammonium residues;

$R^3$ is $COOR^5$ or $CONR^5R^6$;

$R^4$ is $COOR^6$ or $CONR^5R^6$;

$R^5$ and $R^6$ are hydrogen, or are selected from the group consisting of $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, and hetaryl, any of which may be unsubstituted or substituted;

n is 1 to 3 where $R^3$ and $R^4$ are not $COOCH_3$ when $R^1$ and $R^2$ are hydrogen.

2. A 4,4-diarylbutadiene of the formula Ib,

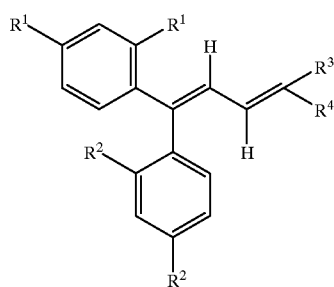

Ib where the diene system has the Z,Z; Z,E; E,Z or E,E configuration or a mixture thereof, and where the variables independently of one another have the following meanings:

$R^1$ and $R^2$ are hydrogen, $C_1$–$C_{20}$-alkyl, $C_1$–$C_{12}$-alkoxy, or $C_1$–$C_{20}$-alkoxycarbonyl;

$R^3$ is $COOR^5$ or $CONR^5R^6$;

$R^4$ is $COOR^6$ or $CONR^5R^6$;

$R^5$ and $R^6$ are hydrogen, or are selected from the group consisting of $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, and hetaryl, any of which may be unsubstituted or substituted;

where $R^3$ and $R^4$ are not $COOCH_3$ when $R^1$ and $R^2$ are hydrogen.

3. A 4,4-diarylbutadiene of the formula Ic,

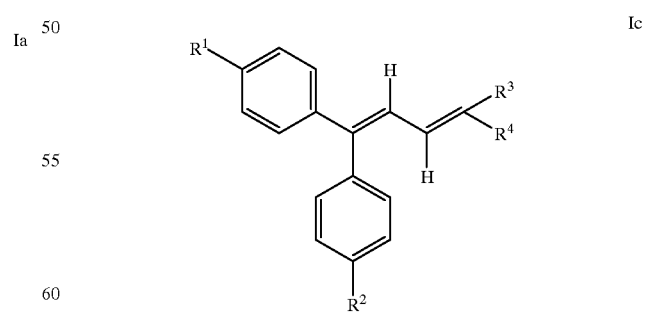

Ic where the diene system has the Z,Z; Z,E; E,Z or E,E configuration or a mixture thereof, and where the variables independently of one another have the following meanings:

$R^1$ and $R^2$ are hydrogen, $C_1$–$C_{20}$-alkyl, $C_1$–$C_{12}$-alkoxy, or $C_1$–$C_{20}$-alkoxycarbonyl;

$R^3$ is $COOR^5$ or $CONR^5R^6$;

$R^4$ is $COOR^6$ or $CONR^5R^6$;

$R^5$ and $R^6$ are hydrogen, or are selected from the group consisting of $C_1$–$C_{20}$-alkyl, $C_2$–$C_{10}$-alkenyl, $C_3$–$C_{10}$-cycloalkyl, $C_7$–$C_{10}$-bicycloalkyl, $C_3$–$C_{10}$-cycloalkenyl, $C_7$–$C_{10}$-bicycloalkenyl, aryl, and hetaryl, any of which may be unsubstituted or substituted;

where $R^3$ and $R^4$ are not $COOCH_3$ when $R^1$ and $R^2$ are hydrogen.

* * * * *